United States Patent
Nickisch et al.

(10) Patent No.: US 9,745,338 B2
(45) Date of Patent: Aug. 29, 2017

(54) PRO-DRUG FORMING COMPOUNDS

(71) Applicant: Evestra, Inc., San Antonio, TX (US)

(72) Inventors: Klaus Nickisch, Berlin (DE); Bindu Santhamma, San Antonio, TX (US); Gulzar Ahmed, San Antonio, TX (US); Frederick Meece, San Antonio, TX (US); Walter Elger, Berlin (DE); Ralf Wyrwa, Rothenstein (DE); Hareesh Nair, San Antonio, TX (US)

(73) Assignee: Evestra, Inc., San Antonio, TX (US)

( * ) Notice: Subject to any disclaimer, the term of this patent is extended or adjusted under 35 U.S.C. 154(b) by 9 days.

(21) Appl. No.: 14/329,322

(22) Filed: Jul. 11, 2014

(65) Prior Publication Data

US 2015/0018322 A1   Jan. 15, 2015

Related U.S. Application Data

(60) Provisional application No. 61/844,985, filed on Jul. 11, 2013.

(51) Int. Cl.
*C07J 43/00* (2006.01)
*C07J 41/00* (2006.01)
*C07J 51/00* (2006.01)

(52) U.S. Cl.
CPC ......... *C07J 43/003* (2013.01); *C07J 41/0072* (2013.01); *C07J 41/0088* (2013.01); *C07J 51/00* (2013.01)

(58) Field of Classification Search
CPC .. C07J 43/003; C07J 41/0088; C07J 41/0072; C07J 51/00
USPC ........ 552/502, 617, 626, 646; 514/176, 181, 514/182; 540/110
See application file for complete search history.

(56) References Cited

U.S. PATENT DOCUMENTS

| | | |
|---|---|---|
| 3,461,118 A | 8/1969 | Edwards |
| 4,360,663 A * | 11/1982 | Asano ............... C07J 1/0074 536/5 |
| 4,615,835 A | 10/1986 | Eisenbrand et al. |
| 5,705,495 A | 1/1998 | Schwarz et al. |
| 6,080,735 A | 6/2000 | Schwarz et al. |
| 6,841,548 B2 | 1/2005 | Schwarz et al. |
| 6,956,031 B2 | 10/2005 | Hillisch et al. |
| 6,958,327 B1 | 10/2005 | Hillisch et al. |
| 7,507,725 B2 | 3/2009 | Elger et al. |
| 7,534,780 B2 * | 5/2009 | Wyrwa ................. C07J 1/00 514/182 |
| 2004/0087565 A1 | 5/2004 | Kosemund et al. |
| 2005/0277625 A1 | 12/2005 | Wyrwa et al. |
| 2007/0135375 A1 | 6/2007 | Wyrwa et al. |
| 2007/0135399 A1 * | 6/2007 | Wyrwa ............... C07J 43/00 514/176 |
| 2007/0219169 A1 | 9/2007 | Becourt et al. |
| 2009/0186869 A1 | 7/2009 | Cottell et al. |
| 2010/0092463 A1 | 4/2010 | Ishikawa et al. |
| 2011/0250542 A1 | 10/2011 | Liu et al. |

FOREIGN PATENT DOCUMENTS

| | | |
|---|---|---|
| CA | 2091268 | 3/1992 |
| EP | 0351561 | 1/1990 |

OTHER PUBLICATIONS

International Search Report for PCT Application No. PCT/US2014/046353 issued Oct. 15, 2014.
Written Opinion for PCT Application No. PCT/US2014/046353 issued Oct. 15, 2014.
Boyle et al. "A new synthesis of difluoromethanesulfonamides—a novel pharmacophore for carbonic anhydrase inhibition" Org. Biomol. Chem., 2005,3, 222-224.
Hassan et al. "Synthesis, antimicrobial and antiviral testing of some new 1-adamantyl analogues" Saudi Pharmaceutical Journal (2010) 18, 123-128.
PubChem CID 42937895, Jul. 20, 2009, pp. 1-3 [online].
PubChem CID 9166052 , Jul. 31, 2006, pp. 1-4 [online].
PubChem CID 799253 , Jul. 9, 2005, pp. 1-5 [online].
PubChem CID 8421747 , Jul. 30, 2006, pp. 1-3 [online].
PubChem CID 56865468 , Mar. 30, 2012, pp. 1-3 [online].
Elger et al. "Sulfamates of various estrogens are prodrugs with increased systemic and reduced hepatic estrogenicity at oral application" J. Steroid Biochem. Molec. Biol. 55, 3-4, Dec. 1995, pp. 395-403.
Li et al. "A Facile Synthesis of 1-Substituted Cyclopropyl sulfonamides" Synlett (2006) 5:725.
Iyer et al. "Inhibition Profiling of Human Carbonic Anhydrase II by High-Throughput Screening of Structurally Diverse, Biologically Active Compounds" Journal of Biomolecular Screening 2006:782-791.
McNatty et al. "Concentration of Oestrogens and Androgens in Human Ovarian Venous Plasma and Follicular Fluid Throughout the Menstrual Cycle" J Endocrinol Oct. 1, 1976 71 77-85.

* cited by examiner

*Primary Examiner* — Sabiha N Qazi
(74) *Attorney, Agent, or Firm* — Meyertons, Hood, Kivlin, Kowert & Goetzel, P.C.

(57) ABSTRACT

Various prodrug compounds having the general structure: Active agent-(acid)-(linker)-$SO_2NR_1R_2$ are described herein. Compounds having this general structure were shown to be more orally active than the unmodified parent molecule.

11 Claims, No Drawings

PRO-DRUG FORMING COMPOUNDS

PRIORITY CLAIM

This application claims priority to U.S. Provisional Application Ser. No. 61/844,985 entitled "Pro-Drug Forming Compounds" filed Jul. 11, 2013, which is incorporated herein by reference in its entirety.

BACKGROUND OF THE INVENTION

1. Field of the Invention

The invention generally relates to derivatives of biologically active molecules which show a higher oral bioavailability and therefore higher biological activity than the original biologically active drug.

2. Description of the Relevant Art

Many endogenic substances, natural products and synthetic substances with therapeutically useful properties exhibit a high "first path" effect when administered orally. This means that these molecules are either quickly metabolized or excreted and as a consequence relative high doses need to be applied to ensure the desired biological effect.

Exemplary compounds that exhibit a high first path effect are sexual steroids such as estrogens and androgens. For example, both natural hormones estradiol and testosterone have a low oral bioavailability that significantly limits their application.

There have been intensive efforts over the years to address this shortcoming.

Simple esters like estradiol 17 benzoate or esters of fatty acids as found in testosterone enanthate lead to somewhat improved oral bioavailability.

Sulfonic acid derivatives have proven to be especially promising. In U.S. Pat. No. 5,705,495 and EP 127 35 90 and EP 128 42 73 estradiol sulfonic acid derivatives were described that show higher estrogenic activity after oral administration than estradiol.

One derivative J955 (estradiol sulfamate) was actually selected for development. J995 exhibited a higher estrogenic activity after oral administration than estradiol and ethinyl estradiol in the Allan Doisy test in ovarectomized female rats (Walter Eiger et. Al J. Steroid Biochem. Molec Biol. Vol 55 395-403 1995). Development of J 995 had to be stopped when it was determined that J995 also acted as an inhibitor of sulfatase in women.

In U.S. Pat. No. 7,507,725 and EP 1 294 402 this concept was broadened and generalized to compounds consisting of three distinct moieties Active-ingredient-(Spacer)-$SO_2NR_1R_2$. These compounds were hypothesized to bind to erythrocytes. The active ingredient could be steroid molecules but also other drugs like diuretics, dopamine agonists and others. The spacer described could consist of either a carbon chain or an aromatic ring or a combination of both.

This concept was later extended to specific substance classes (U.S. Pat. No. 6,841,548; U.S. Pat. No. 6,956,031; U.S. Pat. No. 6,958,327; US 2005/2277625: U.S. Pat. No. 7,534,780; WO 03/104253).

Although the described compounds showed some higher activity than the parent drugs in certain biological tests, the very nature of the described spacer and the sulfonamide moiety lead to compounds with a very low aqueous solubility that limits their use as potential drugs significantly.

SUMMARY OF THE INVENTION

In a first embodiment amino derivatives have the following general formula (I):

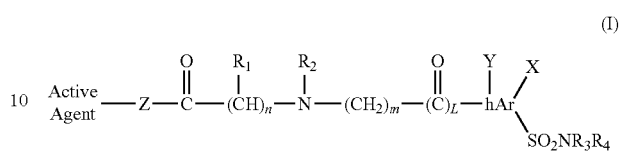

where: n is 0-4; m is 0-4; L is 0-1;
$R_1$ is H, alkyl, cycloalkyl, aryl, alkyl-aryl, heteroaryl, or halogen;
hAr is aryl, heteroaryl, alkyl, alkylaryl, or alkylheteroaryl;
$R_2$ is H, alkyl, cycloalkyl, aryl, heteroaryl, halogen; arylsulfonamide, heteroarylsulfonamide, alkylarylsulfonamide, or alkylheteroarylsulfonamide
$R_1$ and $R_2$ can link together to form a cycloalkyl, or a 3-7 membered ring with up to one heteroatom;
$R_3$ and $R_4$ are each independently H, alkyl, cycloalkyl, aryl, heteroaryl, acyl, cyano, halogen, hydroxy, alkoxy;
X and Y are each independently H, halogen, cyano, hydroxy, alkoxy, alkyl, aryl, heteroaryl;
Z is O or $NR_1$;
$O=C-(CH)_n-R_1$ is in either an R- or S-configuration.

In a second embodiment, oxygen derivatives have the general formula (II)

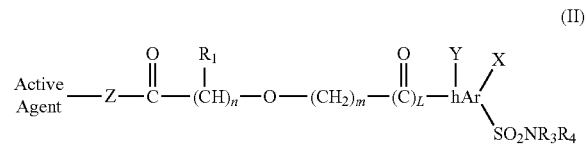

where: n is 0-4; m is 0-4; L is 0-1;
$R_1$ is H, alkyl, cycloalkyl, aryl, heteroaryl, or halogen;
hAr is aryl, or heteroaryl;
$R_3$ and $R_4$ are each independently H, alkyl, cycloalkyl, aryl, heteroaryl, acyl, cyano, halogen, hydroxy, alkoxy;
X and Y are each independently H, halogen, cyano, hydroxy, alkoxy, alkyl, aryl, heteroaryl.
Z is O or $NR_1$;
$O=C-(CH)_n-R_1$ is in either an R- or S-configuration.

In another embodiment, substituted alkyl derivatives have the following general formula (III):

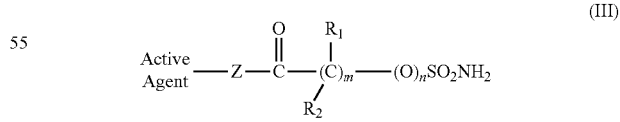

where: n is 0-1; m is 1-4;
Z is O or $NR_1$;
$R_1$ and $R_2$ are each independently halogen, or $R_1$ and $R_2$ are linked together to form a cycloalkyl.

In another aspect, embodiments of the present disclosure provide a pharmaceutical composition that includes the compounds of formulas I, II or III in a pharmaceutically acceptable carrier.

In still another aspect, embodiments of the present disclosure provide a contraceptive product and a hormone replacement therapy product that include the compounds of formulas I and II as set forth below.

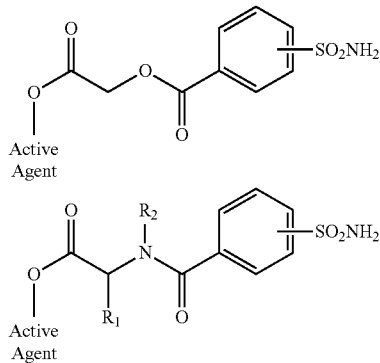

The foregoing has outlined rather broadly the features of the present disclosure in order that the detailed description that follows may be better understood. Additional features and advantages will be described hereinafter, which form the subject of the claims.

DETAILED DESCRIPTION OF THE PREFERRED EMBODIMENTS

It is to be understood the present invention is not limited to particular devices or methods, which may of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

Unless defined otherwise, all technical and scientific terms used herein have the same meaning as commonly understood by one of ordinary skill in the art.

The term "alkyl" as used herein generally refers to a chemical substituent containing the monovalent group $C_nH_{2n}$, where n is an integer greater than zero. In some embodiments n is 1 to 12. The term "alkyl" includes a branched or unbranched monovalent hydrocarbon radical. Examples of alkyl radicals include, but are not limited to: methyl, ethyl, propyl, isopropyl, butyl, iso-butyl, sec-butyl, pentyl, 3-pentyl, hexyl, heptyl, octyl, nonyl, decyl, undecyl, dodecyl. When the alkyl group has from 1-6 carbon atoms, it is referred to as a "lower alkyl." Suitable lower alkyl radicals include, but are not limited to, methyl, ethyl, n-propyl, i-propyl, 2-propenyl (or allyl), n-butyl, t-butyl, and i-butyl (or 2-methylpropyl).

The term "cycloalkyl" denotes groups having an aliphatic chain joined together to form a circular structure. The number of carbons in the aliphatic chain can range from three to 12. Exemplary cycloalkyl groups include cyclopropyl-, cyclobutyl, cyclopentyl and cyclohexyl.

The term "alkoxy" generally refers to an —OR group, where R is a lower alkyl, substituted lower alkyl, aryl, substituted aryl, aralkyl or substituted aralkyl. Suitable alkoxy radicals include, but are not limited to, methoxy, ethoxy, phenoxy, t-butoxy, methoxyethoxy, and methoxymethoxy.

The term "halogen" is used herein to refer to fluorine, bromine, chlorine and iodine atoms.

The term "hydroxyl" is used herein to refer to the group —OH.

The term "aryl" is used to refer to an aromatic substituent which may be a single ring or multiple rings which are fused together, linked covalently, or linked to a common group such as an ethylene moiety. Aromatic ring(s) include but are not limited to phenyl, naphthyl, biphenyl, diphenylmethyl, and 2,2-diphenyl-1-ethyl. The aryl group may also be substituted with substituents including, but not limited to, alkyl groups, halogen atoms, nitro groups, carboxyl groups, alkoxy, and phenoxy to give a "substituted aryl group." Substituents may be attached at any position on the aryl radical which would otherwise be occupied by a hydrogen atom.

The term "heterocycle" as used herein generally refers to a closed-ring structure, in which one or more of the atoms in the ring is an element other than carbon. Heterocycle may include aromatic compounds or non-aromatic compounds. Heterocycles may include rings such as thiophene, pyridine, isoxazole, phthalimide, pyrazole, indole, furan, or benzo-fused analogs of these rings. Examples of heterocycles include tetrahydrofuran, morpholine, piperidine, pyrrolidine, and others. In some embodiments, "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms (e.g., N, O, and S) and wherein the nitrogen and sulfur heteroatoms may optionally be oxidized, and the nitrogen may optionally be quaternized, and including any bicyclic group in which any of the above-defined heterocyclic rings is fused to a benzene ring. In some embodiments, heterocycles may include cyclic rings including boron atoms. The heterocyclic ring may be attached to its pendant group at any heteroatom or carbon atom that results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzofuranyl, benzothiophenyl, carbazole, chromanyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl, oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, quinazolinyl, quinolinyl, quinoxalinyl, quinuclidinyl, carbolinyl, tetrahydrofuranyl, tetrahydroisoquinolinyl, tetrahydroquinolinyl, tetrazolyl, thianthrenyl, thiazolyl, thienyl, thiophenyl, triazinyl, xanthenyl. Also included are fused ring and spiro compounds containing, for example, the above heterocycles. The term "heteroaryl" has an equivalent meaning as heterocycle, and these terms are used interchangeably.

The term "pharmaceutically acceptable salts" includes salts prepared from by reacting pharmaceutically acceptable non-toxic bases or acids, including inorganic or organic bases, with inorganic or organic acids. Pharmaceutically acceptable salts may include salts derived from inorganic bases including aluminum, ammonium, calcium, copper, ferric, ferrous, lithium, magnesium, manganic salts, manganous, potassium, sodium, zinc, etc. Examples include the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, etc.

LIST OF ABBREVIATIONS

AcOH—acetic acid
Boc—tertiary butyl carbamate
Cbz—benzyl carbamate
DCC—dicyclohexylcarbodiimide
DCM—dichloromethane
DIC—diisopropylcarbodiimide
DMAP—N,N-dimethyl-4-aminopyridine
DMF—dimethylformamide
DMSO—dimethyl sulfoxide
EDCI—N-(3-dimethylaminopropyl)-N'-ethylcarbodiimide hydrochloride
EtOAc—ethyl acetate
HOBt—1-hydroxybenzotriazole hydrate
HPLC—high pressure liquid chromatography
Hunig's base—diisopropylethylamine
IR—infrared spectrometry
MPLC—medium pressure liquid chromatography
NMR—nuclear magnetic resonance
p-TSA—para-toluenesulfonic acid
PDC—pyridinium dichromate
TBAI—tetrabutylammonium iodide
TBAF—tetrabutylammonium fluoride
TBS—tertiarybutyldimethylsilyl
TBSCl—tertiarybutyldimethylsilyl chloride
THF—tetrahydrofuran
TLC—thin layer chromatography The embodiments described herein address the shortcomings of prior compounds and describe pro-drug molecules that show significant higher oral activity than the original molecules.

It was hypothesized that including heteroatoms like nitrogen or oxygen in the linker would increase solubility and therefore oral activity of the molecules. Especially suitable in this context could be amino acids. Esters of amino acids with steroids have been described. In CN 102127137 and CN 102079771 amino acid ester with estrogens are disclosed that have anti-tumor activity and exhibit good water solubility. In FR 2774989 estradiol peptides are described that show anti-tumor and cytotoxic activity. In DE 4029499 estradiol diphosphonate derivatives are describe for the treatment of osteoporosis. In EP 351561 estratrienediol derivatives are described as neoplastic compounds and in U.S. Pat. No. 4,615,835 steroid esters with nitrosocarbamoylamino acids are described with high tumor activity.

In this invention compounds are claimed that have the following moieties:

Active ingredient-(acid)-(linker)-$SO_2NR_1R_2$.

The active ingredient can be any active ingredient that has at least at last one hydroxy or amino group. The active ingredient is preferentially selected from androgens, anabolic agents, antiandrogens, estrogens, progestins, or CNS active compounds.

In one embodiment, the active ingredient is an androgen like testosterone, whereby the functional group is the 17-hydroxy function. An exemplary androgen is 7α, 11β-dimethyl-estra-4,9-dien-17-ol, whereby the functional group is the 17 hydroxy function.

In another embodiment, the active ingredient is an estrogen. Exemplary estrogens are estradiol or estriol, whereby the functional group is the 16 or 17 hydroxy group.

In an embodiment, the active ingredient is a progestin such as trimegestone and the functional group is the 21 hydroxy group.

The compounds described herein act as a pro-drug that enables an active agent to be taken up by erythrocytes. The uptake of these compounds by erythrocytes is made possible by a group of the formula —$SO_2NR_3NR_4$; wherein $R_3$ and $R_4$, independently from each other, are H, alkyl, cycloalkyl, aryl, heteroaryl, acyl, cyano, halogen, hydroxy, or alkoxy. The inventive pro-drugs enable active agents such as endogenic substances, natural substances and synthetic substances with therapeutically useful properties which have a high "first path effect", to be administered orally effectively or significantly improve the oral activity thereof.

In a first embodiment amino derivatives have the following general formula (I):

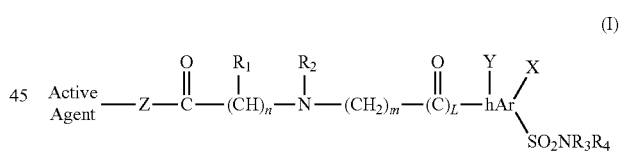

(I)

where: n is 0-4; m is 0-4; L is 0-1;

$R_1$ is H, alkyl, cycloalkyl, aryl, alkyl-aryl, heteroaryl, or halogen;

hAr is aryl, heteroaryl, alkyl, alkylaryl, or alkylheteroaryl;

$R_2$ is H, alkyl, cycloalkyl, aryl, heteroaryl, halogen; arylsulfonamide, heteroaryl sulfonamide, alkylarylsulfonamide, or alkylheteroarylsulfonamide $R_1$ and $R_2$ can link together to form a cycloalkyl, or a 3-7 membered ring with up to one heteroatom;

$R_3$ and $R_4$ are each independently H, alkyl, cycloalkyl, aryl, heteroaryl, acyl, cyano, halogen, hydroxy, alkoxy;

X and Y are each independently H, halogen, cyano, hydroxy, alkoxy, alkyl, aryl, heteroaryl;

Z is O or $NR_1$;

O=C—(CH)$_n$—$R_1$ is in either an R- or S-configuration.

In a second embodiment, oxygen derivatives have the general formula (II)

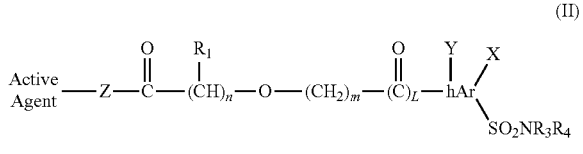

where: n is 0-4; m is 0-4; L is 0-1;
$R_1$ is H, alkyl, cycloalkyl, aryl, heteroaryl, or halogen;
hAr is aryl, heteroaryl, alkyl, alkylaryl, or alkylheteroaryl;
$R_3$ and $R_4$ are each independently H, alkyl, cycloalkyl, aryl, heteroaryl, acyl, cyano, halogen, hydroxy, or alkoxy;
X and Y are each independently H, halogen, cyano, hydroxy, alkoxy, alkyl, aryl, heteroaryl.
Z is O or $NR_1$;
$O=C-(CH)_n-R_1$ is in either an R- or S-configuration.

In another embodiment, substituted alkyl derivatives have the following general formula (III):

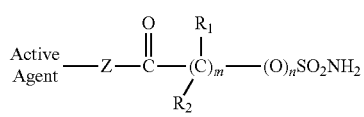

where: n is 0-1; m is 1-4;
Z is O or $NR_1$;
$R_1$, $R_2$ are each independently halogen, or $R_1$ and $R_2$ are linked together to form a cycloalkyl.

In another embodiment, substituted heteroaryl derivatives have the following general formula (IV):

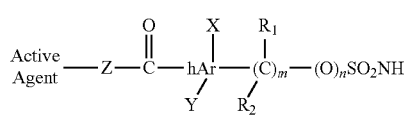

where: n is 0-1; m is 1-4;
$R_1$ and $R_2$ are each independently H, halogen, alkyl, alkenyl, cycloalkyl, alkoxy, acyl hAr is aryl, heteroaryl;
Z is O or $NR_1$;
X and Y are each independently H, halogen, cyano, hydroxyl, alkoxy, alkyl, cycloalkyl, aryl, heteroaryl, or OAc.

In another embodiment, substituted heteroaryl derivatives have the following general formula (V):

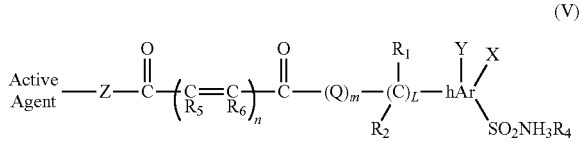

where: n is 0-2; m is 0-1; L is 0-4;
$R_1$, $R_2$ are each independently H, halogen, cycloalkyl, alkyl, aryl, heteroaryl, acyl, cyano, halogen, hydroxyl, or alkoxy;
$R_1$ and $R_2$ can link together to form a cycloalkyl;
$R_3$ and $R_4$ are each independently H, alkyl, cycloalkyl, aryl, heteroaryl, acyl, cyano, halogen, hydroxy, or alkoxy;
$R_5$ and $R_6$ are each independently H, alkyl, aryl, halogen, alkoxy, cycloalkyl;
hAr is aryl, heteroaryl;
Z is O or $NR_1$;
X and Y are each independently H, halogen, cyano, hydroxyl, alkoxy, alkyl, aryl, or heteroaryl;
Q is O.

In another embodiment, substituted heteroaryl derivatives have the following general formula (VI):

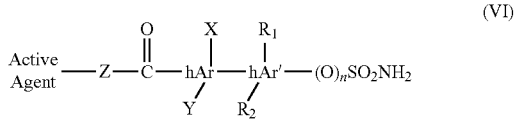

where: n is 0-1;
$R_1$ and $R_2$ are each independently H, halogen, alkyl, alkenyl, cycloalkyl, cyano, alkoxy or acyl;
hAr is vinyl, acetylene, aryl, heteroaryl
hAr' is aryl, heteroaryl;
Z is O or $NR_1$;
X and Y are each independently H, halogen, cyano, hydroxyl, alkoxy, alkyl, cycloalkyl, aryl, heteroaryl, or acyl.

In another aspect, embodiments of the present disclosure provide a pharmaceutical composition that includes the compounds of formulas I-VI in a pharmaceutically acceptable carrier.

Specific embodiments of the present disclosure provide a contraceptive product and a hormone replacement therapy product that include the compounds of formulas I and II as set forth below.

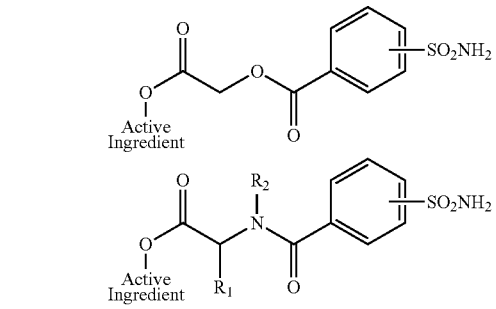

The above described compounds may be formulated into a pharmaceutical composition that includes a compound having any one of formulas (I)-(VI) and a pharmaceutically acceptable carrier. Additional excipients may be present depending on the route of administration.

Any suitable route of administration may be employed for providing a patient with an effective dosage of the compounds described herein. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In certain embodiments, it may be advantageous that the compositions described herein be administered orally.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Prodrug Patent Experimental:

(13S,17S)-3-hydroxy-13-methyl-7,8,9,11,12,13,14,15, 16,17-decahydro-6H-cyclopenta[a]phenanthren-17-yl 3-sulfamoylbenzoate 1A was synthesized according the literature (U.S. Pat. No. 7,507,725 and EP 1 294 402).

(13S,17S)-17-hydroxy-13-methyl-7,8,9,11,12,13,14,15, 16,17-decahydro-6H-cyclopenta[a]phenanthren-3-yl sulfamate J995 was synthesized according the literature (U.S. Pat. No. 5,705,495, EP 127 35 90 and EP 128 42 73).

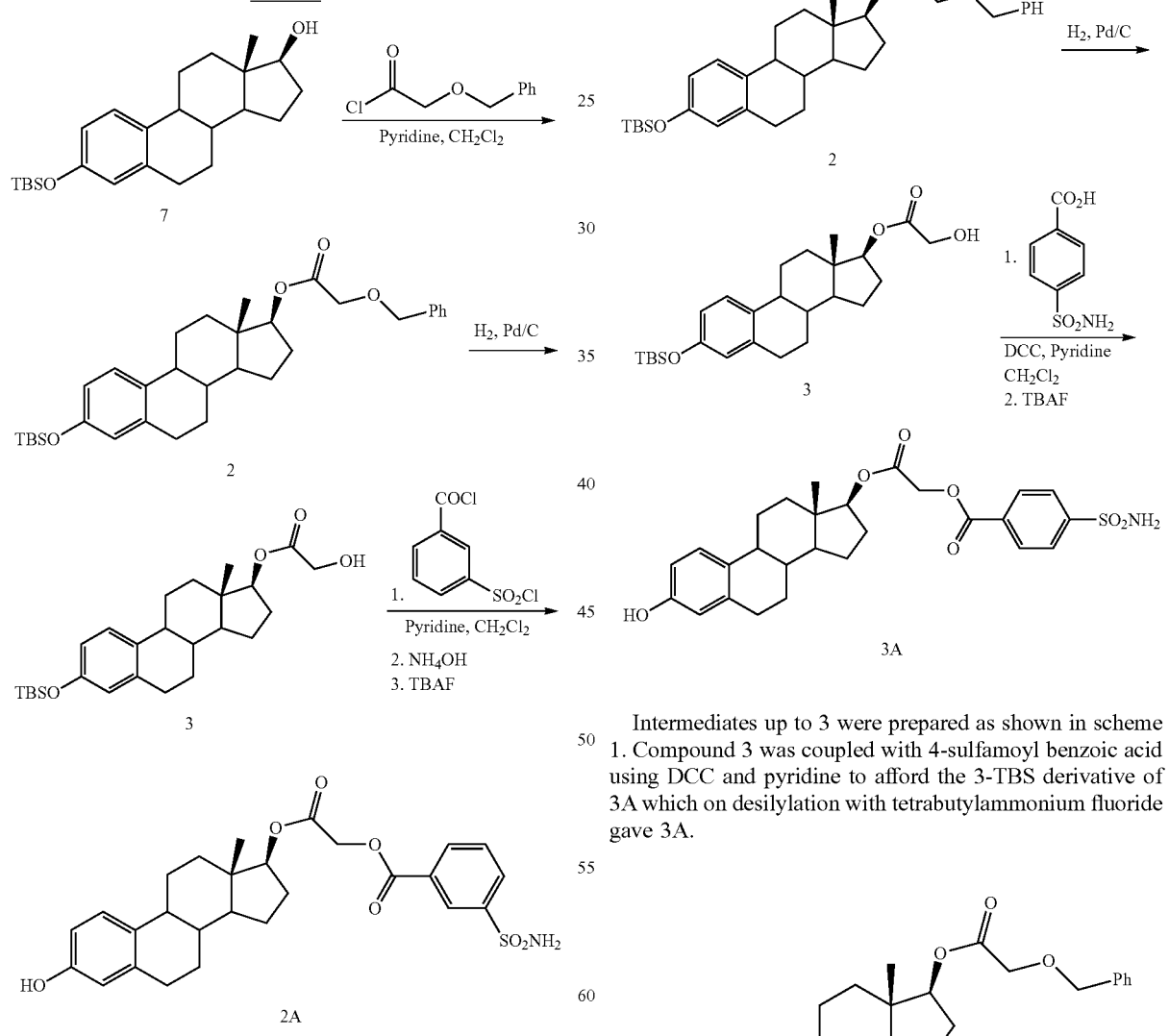

2A may be synthesized as represented in Scheme 1. Estradiol 3-TBS ether 7 was treated with benzyloxy acetyl chloride in presence of pyridine to give the ester 2, which upon debenzylation afforded compound 3. Esterification of 3 with 3-chlorosulfonyl benzoyl chloride in presence of pyridine furnished the 3-TBS protected E2 which was de-silylated with tetrabutylammonium fluoride to afford 2A.

3A may be synthesized as shown in the following Scheme 2.

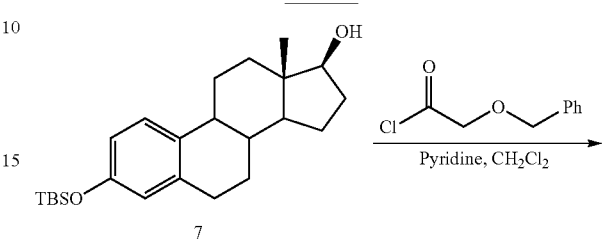

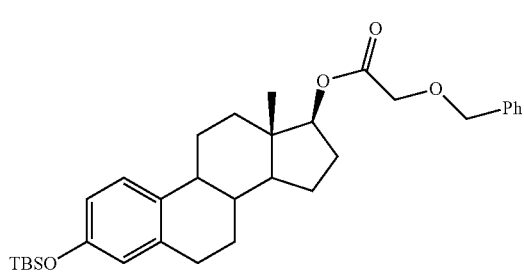 [SMILES: CC(C)(C)[Si](C)(C)Oc1ccc2c(c1)CCC1C2CC[C@@]2(C)C1CC[C@@H]2OC(=O)COCc1ccccc1]

Intermediates up to 3 were prepared as shown in scheme 1. Compound 3 was coupled with 4-sulfamoyl benzoic acid using DCC and pyridine to afford the 3-TBS derivative of 3A which on desilylation with tetrabutylammonium fluoride gave 3A.

(13S,17S)-3-(tert-butyldimethylsilyloxy)-13-methyl-7,8,9,11,12,13,14,15,16,17-decahydro-6H-cyclopenta[a]phenanthren-17-yl 2-(benzyloxy)acetate (2)

Benzyloxyacetyl chloride (0.31 g, 1.67 mmol) was added to a solution of Steroid 7 (0.5 g, 1.29 mmol) and pyridine (0.13 g, 1.67 mmol) in anhydrous dichloromethane (10 mL) at 0° C. After stirring this solution for 45 min, water was added. The reaction mixture was extracted three times with dichloromethane. The combined organic layers were washed with sat. NaHCO$_3$, brine and dried over anhy. Na$_2$SO$_4$. The solvent was removed under vacuum and the crude product was purified by column chromatography (SiO$_2$, hexane-ethyl acetate) to give 2 (640 mg, 93%). $^1$H NMR (δ, CDCl$_3$, 300 MHz): 7.27-7.38 (m, 5H, ArH), 7.13 (d, J=8.4 Hz, 1H, ArH), 6.62 (dd, J$_1$=8.4 Hz, J$_2$=2.6 Hz, 1H, ArH), 6.55 (d, J=2.4 Hz, 1H, ArH), 4.82 (t, J=8.7 Hz, 1H, —CH), 4.65 (s, 2H, —O—(CH$_2$), 4.11 (s, 2H, —O—(CH$_2$), 2.81 (m, 2H, —CH$_2$), 0.97 (s, 9H, Si—CH$_3$), 0.82 (s, 3H, —CH$_3$), 0.18 (s, 6H, Si—CH$_3$).

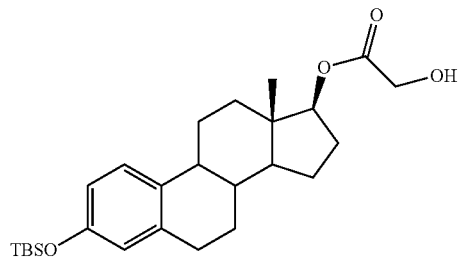 [SMILES: CC(C)(C)[Si](C)(C)Oc1ccc2c(c1)CCC1C2CC[C@@]2(C)C1CC[C@@H]2OC(=O)CO]

(13S,17S)-3-(tert-butyldimethylsilyloxy)-13-methyl-7,8,9,11,12,13,14,15,16,17-decahydro-6H-cyclopenta[a]phenanthren-17-yl 2-hydroxyacetate (3)

A solution of compound 2 (0.64 g, 1.19) in ethyl acetate was mixed with 5% palladium on carbon (0.06 g, 0.6 mmol) and was hydrogenated at a pressure of 20 psi for 1 h. The solution was filtered to remove the catalyst and was evaporated to dryness. The crude obtained was purified by column chromatography (SiO$_2$, Hexane-EtOAc) to afford 3 (0.47 g, 89%). $^1$H NMR (δ, CDCl$_3$, 300 MHz): 7.21 (d, J=8.4 Hz, 1H, ArH), 6.60 (dd, J$_1$=8.4 Hz, J$_2$=2.6 Hz, 1H, ArH), 6.55 (d, J=2.4 Hz, 1H, ArH), 4.81 (t, J=8.8 Hz, 1H, —CH), 4.15 (d, J=2.4 Hz, 2H, —OCH$_2$), 2.80 (m, 2H, —CH$_2$), 0.97 (s, 9H, Si—CH), 0.82 (s, 3H, —CH$_3$), 0.18 (s, 6H, Si—CH).

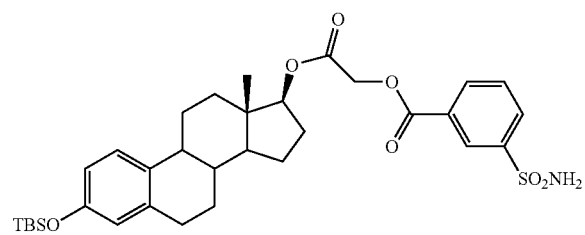 [SMILES: CC(C)(C)[Si](C)(C)Oc1ccc2c(c1)CCC1C2CC[C@@]2(C)C1CC[C@@H]2OC(=O)COC(=O)c1cccc(S(N)(=O)=O)c1]

2-((13S,17S)-3-(tert-butyldimethylsilyloxy)-13-methyl-7,8,9,11,12,13,14,15,16,17-decahydro-6H-cyclopenta[a]phenanthren-17-yloxy)-2-oxoethyl 3-sulfamoylbenzoate A solution of 3 (0.2 g, 0.45 mmol) and pyridine (0.05 g, 0.6 mmol) in dichloromethane (10 mL) at −20° C. was treated dropwise with a solution of 3-sulfamoyl benzoyl chloride (0.14 g, 0.6 mmol) in dichloromethane. After stirring for 30 min at −20° C., the reaction was warmed to 8° C. and quenched with NH$_4$OH solution (3 mL) and stirred for another 30 min. The reaction mixture was extracted three times with dichloromethane. The combined organic layers were washed with water, brine and dried over anhydrous Na$_2$SO$_4$. The solvent was removed under vacuum and the crude was purified by column chromatography (SiO$_2$, hexane-EtOAc) to give the 3-TBS protected 2A (0.24 g, 85%). $^1$H NMR (δ, CDCl$_3$, 300 MHz): 8.64-8.66 (m, 1H, ArH), 8.28-8.31 (m, 1H, ArH), 8.12-8.16 (m, 1 h, ArH), 7.63 (t, J=7.9 Hz, 1H, ArH), 7.09 (d, J=8.4 Hz, 1H, ArH), 6.60 (dd, J$_1$=8.4 Hz, J$_2$=2.6 Hz, 1H, ArH), 6.54 (d, J=2.4 Hz, 1H, ArH), 4.89 (s, 2H, —OCH$_2$), 4.80 (t, J=8.8 Hz, 1H, —CH), 2.80 (m, 2H, —CH$_2$), 0.97 (s, 9H, Si—CH$_3$), 0.79 (s, 3H, —CH$_3$), 0.18 (s, 6H, Si—CH$_3$).

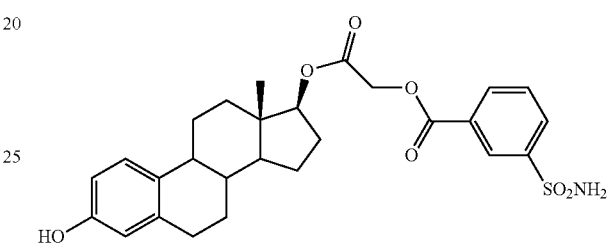

2-((13S,17S)-3-hydroxy-13-methyl-7,8,9,11,12,13,14,15,16,17-decahydro-6H-cyclopenta[a]phenanthren-17-yloxy)-2-oxoethyl 3-sulfamoylbenzoate (2A)

A solution of the 3-TBS ether of 2A (0.24 g, 0.38 mmol) in anhydrous THF (10 mL) was treated with tetrabutylammonium fluoride (0.13 g, 0.42 mmol). After stirring for 1 h at rt, water was added and extracted three times with EtOAc. The combined organic layers were washed with water, brine and dried over anhydrous Na$_2$SO$_4$. The solvent was removed under vacuum and the crude was purified by column chromatography (SiO$_2$, hexane-EtOAc) to give 2A (0.16 g, 82%). IR (cm$^{-1}$): 3352, 3257, 2926, 2858, 1727, 1499, 1221, 1159, 1127, 1039, 750. $^1$H NMR (δ, CDCl$_3$, 300 MHz): 8.65-8.66 (m, 1H, ArH), 8.28-8.31 (m, 1H, ArH), 8.12-8.16 (m, 1 h, ArH), 7.63 (t, J=7.8 Hz, 1H, ArH), 7.12 (d, J=8.4 Hz, 1H, ArH), 6.61 (dd, J$_1$=8.4 Hz, J$_2$=2.6 Hz, 1H, ArH), 6.54 (d, J=2.4 Hz, 1H, ArH), 5.08 (s, 2H, —NH$_2$), 4.95 (s, 1H, —OH), 4.83 (s, 2H, —OCH$_2$), 4.80 (t, J=8.9 Hz, 1H, —CH), 2.79 (m, 2H, —CH$_2$), 0.73 (s, 3H, —CH$_3$). $^{13}$C NMR (δ, CDCl$_3$, 75 MHz): 167.64, 164.50, 153.38, 138.09, 133.79, 132.33, 130.90, 130.44, 129.52, 127.93, 126.48, 115.23, 112.70, 84.23, 61.64, 49.61, 43.66, 43.13, 38.47, 36.81, 29.49, 27.40, 27.09, 26.12, 23.20, 12.03.

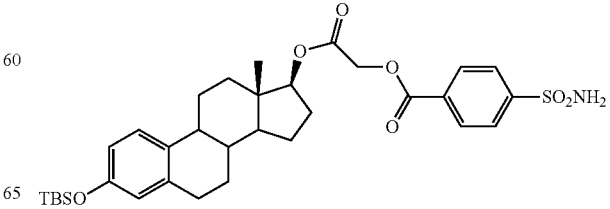

2-((13S,17S)-3-(tert-butyldimethylsilyloxy)-13-methyl-7,8,9,11,12,13,14,15,16,17-decahydro-6H-cyclopenta[a]phenanthren-17-yloxy)-2-oxoethyl 4-sulfamoylbenzoate To a solution of 3 (0.22 g, 0.5 mmol) and 4-sulfamoyl benzoic acid (0.24 g, 1.15 mmol) in pyridine (10 mL) was added p-TsOH (0.08 g, 0.5 mmol) followed by a 1M solution DCC in dichloromethane (0.24 g, 1.15 mmol). After stirring at rt for 72 h, water was added and the pH of the reaction was brought to 7 by the addition of 4N hydrochloric acid. The reaction mixture was extracted three times with ethyl acetate and the combined organic layers were washed with water, brine and dried over anhydrous $Na_2SO_4$. The solvent was removed under vacuum and the crude was purified by column chromatography ($SiO_2$, hexane-EtOAc) to give the 3-TBS ether of 3A (0.27 g, 86%). $^1$H NMR (δ, $CDCl_3$, 300 MHz): 8.23 (d, J=8.5 Hz, 2H, ArH), 8.02 (d, J=8.5 Hz, 2H, ArH), 7.10 (d, J=8.4 Hz, 1H, ArH), 6.61 (dd, $J_1$=8.4 Hz, $J_2$=2.5 Hz, 1H, ArH), 6.53 (d, J=2.4 Hz, 1H, ArH), 4.89 (s, 2H, —$OCH_2$), 4.80 (t, J=8.9 Hz, 1H, —CH), 2.80 (m, 2H, —$CH_2$), 0.97 (s, 9H, Si—$CH_3$), 0.78 (s, 3H, —$CH_3$), 0.18 (s, 6H, Si—$CH_3$), 0.18 (s, 6H, Si—$CH_3$).

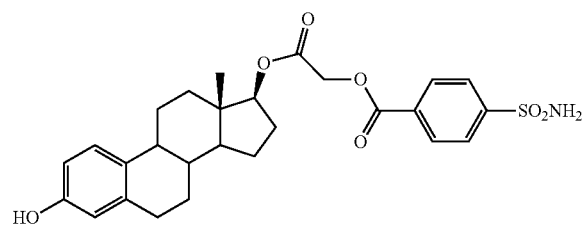 [SMILES: C[C@]12CCC3c4ccc(O)cc4CCC3C1CC[C@@H]2OC(=O)COC(=O)c1ccc(S(N)(=O)=O)cc1]

2-((13S,17S)-3-hydroxy-13-methyl-7,8,9,11,12,13,14,15,16,17-decahydro-6H-cyclopenta[a]phenanthren-17-yloxy)-2-oxoethyl 4-sulfamoylbenzoate (2A)

As described for 2A, the TBS group was removed by treating 3-TBS ether of 3A (0.26 g, 0.4 mmol) with $TBAF·3H_2O$ (0.3 g, 0.45 mmol) to afford 3A (0.2 g, 95%). IR ($cm^{-1}$): 3386, 3265, 2930, 2853, 1731, 1549, 1225, 1167, 1122, 1039, 765. $^1$H NMR (δ, $CDCl_3$, 300 MHz): 8.15 (d, J=8.5 Hz, 2H, ArH), 7.95 (d, J=8.5 Hz, 2H, ArH), 7.05 (d, J=8.4 Hz, 1H, ArH), 6.55 (dd, $J_1$=8.4 Hz, $J_2$=2.5 Hz, 1H, ArH), 6.49 (d, J=2.4 Hz, 1H, ArH), 4.91 (s, 2H, —$OCH_2$), 4.74 (t, J=8.8 Hz, 1H, —CH), 2.80 (m, 2H, —$CH_2$), 0.73 (s, 3H, —$CH_3$). $^{13}$C NMR (δ, $CDCl_3$, 75 MHz): 167.59, 164.68, 154.146.91, 137.91, 133.79, 132.40, 131.30, 130.36, 126.23, 115.09, 112.61, 84.17, 61.54, 49.48, 49.38, 49.10, 48.81, 48.68, 43.55, 42.99, 38.42, 36.68, 33.57, 29.39, 27.26, 27.03, 25.99, 25.42, 24.73, 23.06, 11.86.

2-((13S,16R,17R)-16-(tert-butyldimethyl silyloxy)-3-hydroxy-13-methyl-7,8,9,11,12,13,14,15,16,17-decahydro-6H-cyclopenta[a]phenanthren-17-yloxy)-2-oxoethyl 3-sulfamoylbenzoate A solution of 25 (0.7 g, 1.2 mmol) and pyridine (0.19 g, 2.43 mmol) in dichloromethane (10 mL) at −20° C. was treated drop wise with a solution of 3-sulfamoyl benzoyl chloride (0.58 g, 2.43 mmol) in dichloromethane. After stirring for 30 min at −20° C., the reaction was warmed to 8° C. and quenched with $NH_4OH$ solution (3 mL) and stirred for another 30 min. The reaction mixture was extracted three times with dichloromethane. The combined organic layers were washed with water, brine and dried over anhydrous $Na_2SO_4$. The solvent was removed under vacuum and the crude was purified by column chromatography ($SiO_2$, hexane-EtOAc) to give the 3 and 16-TBS protected 24A (0.78 g, 84%). This compound (0.28 g, 0.37 mmol) was treated with TBAF (0.12 g, 0.37 mmol) to afford the 16-TBS ether of 24A (0.2 g, 84%). $^1$H NMR ($CDCl_3$-DMSO, 300 MHz): 8.66-8.67 (m, 1H, ArH), 8.30-8.33 (m, 1H, ArH), 8.13-8.15 (m, 1 h, ArH), 7.65 (t, J=7.8 Hz, 1H, ArH), 7.11 (d, J=8.4 Hz, 1H, ArH), 6.59 (dd, $J_1$=8.4 Hz, $J_2$=2.2 Hz, 1H, ArH), 6.55 (d, J=2.2 Hz, 1H, ArH), 4.96 (s, 2H, —$OCH_2$), 4.52 (d, J=4.7 Hz, 1H, —CH), 4.06 (m, 1H, —CH), 2.73 (m, 2H, —$CH_2$), 0.89 (s, 9H, Si—$CH_3$) 0.74 (s, 3H, —$CH_3$), 0.05 (s, 6H, Si—$CH_3$).

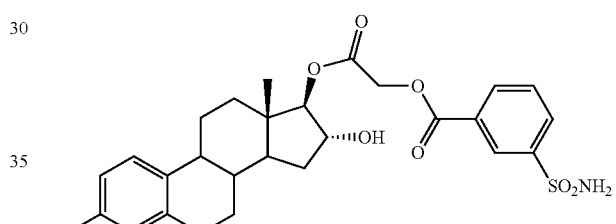

2-((13S,16R,17R)-3,16-dihydroxy-13-methyl-7,8,9,11,12,13,14,15,16,17-decahydro-6H-cyclopenta[a]phenanthren-17-yloxy)-2-oxoethyl 3-sulfamoylbenzoate 16-TBS protected 24A (0.2 g, 0.3 mmol) was treated with 4N HCl (0.02 g, 0.5 mmol) to afford 24A (0.16 g, 97%). IR ($cm^{-1}$): 3346, 2933, 2856, 1737, 1728, 1342, 1225, 1168, 1132, 913, 731. $^1$H NMR ($CDCl_3$-DMSO, 300 MHz): 8.54-8.56 (m, 1H, ArH), 8.19-8.22 (m, 1H, ArH), 8.07-8.10 (m, 1 h, ArH), 7.58 (t, J=7.9 Hz, 1H, ArH), 7.03 (d, J=8.6 Hz, 1H, ArH), 6.56 (dd, $J_1$=8.4 Hz, $J_2$=2.2 Hz, 1H, ArH), 6.49 (d, J=2.2 Hz, 1H, ArH), 4.90 (s, 2H, —O—($CH_2$), 4.52 (d, J=4.7 Hz, 1H, —CH), 4.06 (m, 1H, —CH), 2.73 (m, 2H, —$CH_2$), 0.74 (s, 3H, —$CH_3$).

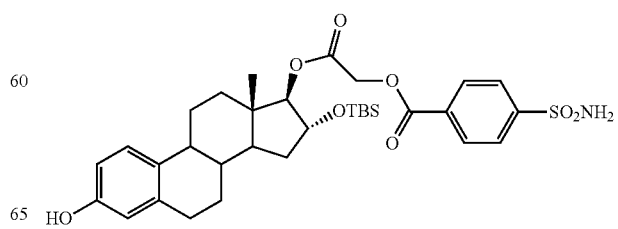

2-((13S,16R,17R)-16-(tert-butyldimethylsilyloxy)-3-hydroxy-13-methyl-7,8,9,11,12,13,14,15,16,17-decahydro-6H-cyclopenta[a]phenanthren-17-yloxy)-2-oxoethyl 4-sulfamoylbenzoate To a solution of 25 (1.1 g, 1.9 mmol) and 4-sulfamoyl benzoic acid (0.95 g, 4.4 mmol) in pyridine (10 mL) was added p-TsOH (0.3 g, 1.71 mmol) followed by a 1M solution DCC in dichloromethane (4.4 mL, 1.15 mmol). After stirring at rt for 72 h, water was added and the pH of the reaction was brought to 7 by the addition of 4N hydrochloric acid. The reaction mixture was extracted three times with ethyl acetate and the combined organic layers were washed with water, brine and dried over anhydrous $Na_2SO_4$. The solvent was removed under vacuum and the crude was purified by column chromatography ($SiO_2$, hexane-EtOAc) to give the 3 and 16-TBS ether of 25A (0.71 g, 51%). This compound (0.51 g, 0.67 mmol) was treated with TBAF (0.2 g, 0.67 mmol) to give the 16-TBS ether of 25A (0.4 g, 93%). $^1$H NMR ($CDCl_3$-DMSO, 300 MHz): 8.23-8.26 (m, 2H, ArH), 8.01-8.04 (m, 2H, ArH), 7.12 (d, J=8.4 Hz, 1H, ArH), 6.63 (dd, $J_1$=8.1 Hz, $J_2$=2.1 Hz, 1H, ArH), 6.55 (d, J=2.4 Hz, 1H, ArH), 4.91-4.93 (m, 5H, —$OCH_2$, —OH, —$NH_2$), 4.68 (s 1H, —CH), 4.29-0.32 (m, 1H, —CH), 2.81 (m, 2H, —$CH_2$), 0.89 (s, 9H, Si—$CH_3$) 0.77 (s, 3H, —$CH_3$), 0.05 (s, 6H, Si—$CH_3$).

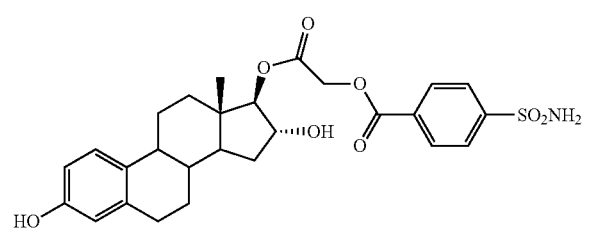 [SMILES: C[C@]12CCC3c4ccc(O)cc4CCC3C1C[C@@H](O)[C@@H]2OC(=O)COC(=O)c1ccc(S(N)(=O)=O)cc1]

2-((13S,16R,17R)-3,16-dihydroxy-13-methyl-7,8,9,11,12,13,14,15,16,17-decahydro-6H-cyclopenta[a]phenanthren-17-yloxy)-2-oxoethyl 4-sulfamoylbenzoate As described for 24A, the 16-TBS ether of 25A (0.45 g, 0.69 mmol) was treated with 4N HCl (0.07 g, 2.07 mmol) to afford 25A (0.32 g, 87%). IR ($cm^{-1}$): 3485, 3409, 2929, 2859, 1740, 1720, 1424, 1345, 1221, 1178, 1117, 913, 608. $^1$H NMR ($CDCl_3$-DMSO, 300 MHz): 8.19 (d, J=8.5 Hz, 2H, ArH), 7.99 (d, J=8.5 Hz, 2H, ArH), 7.61 (bs, 1H, OH), 7.02 (d, J=8.6 Hz, 1H, ArH), 6.51 (dd, $J_1$=8.1 Hz, $J_2$=2.1 Hz, 1H, ArH), 6.42 (d, J=2.4 Hz, 1H, ArH), 5.02 (s, 3H, —$OCH_2$, —OH), 4.72 (d, J=5.5 Hz, 1H, —CH), 4.11 (m, 1H, —CH), 2.68 (m, 2H, —$CH_2$), 0.69 (s, 3H, —$CH_3$).

Scheme 5

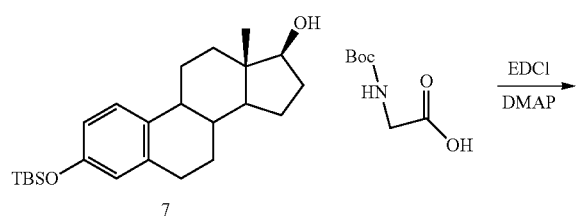

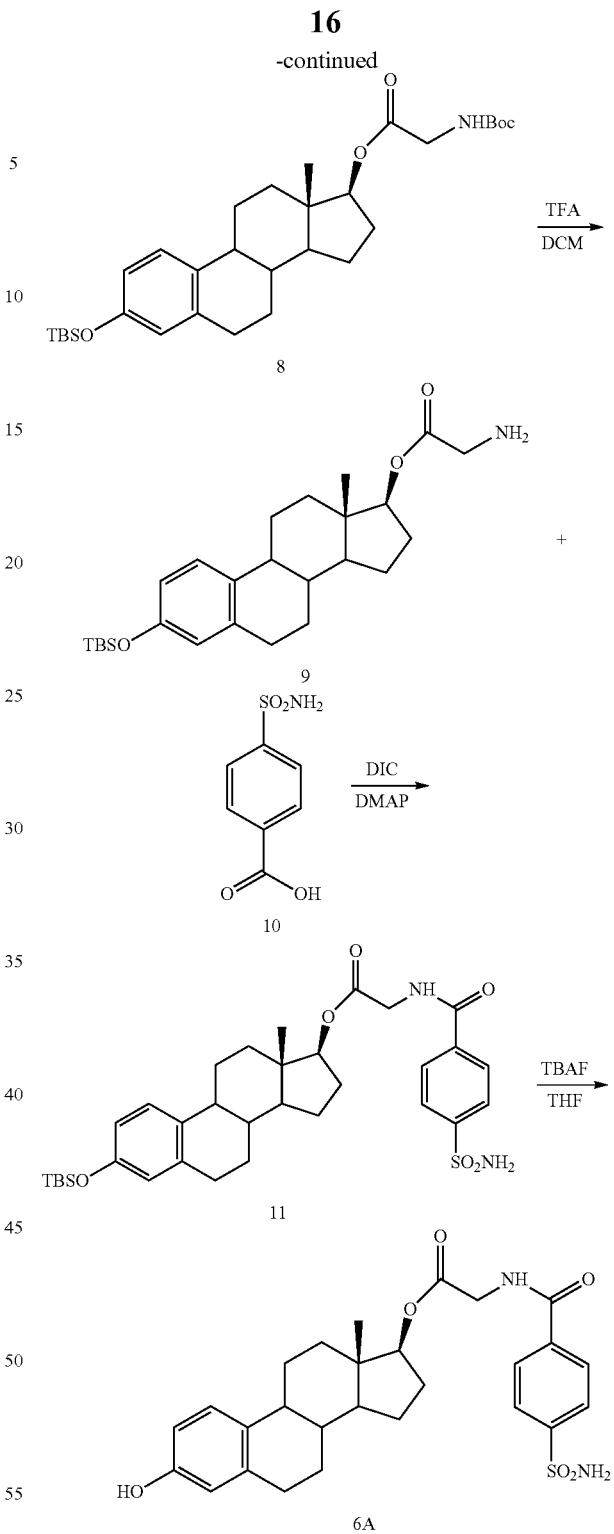

Boc-Glycine-OH (2.0 g, 2 eq.) was treated with 1-ethyl-3-(3-dimethylaminopropyl)carbodiimide (EDCI, 2.2 g, 2 eq.) in DCM (30 mL) for 1 hour at rt. Estradiol 7 (2.1 g, 1 eq.) and 4-dimethylaminopyridine (DMAP, 0.7 g, 1 eq) were then added and the resulting mixture was stirred at rt for 20 h. The reaction was concentrated and the residue was purified by silica gel chromatography using 60-100% DCM in hexanes as eluent to afford the ester product as white solid 8 (2.1 g, 68% yield).

The ester 8 (2.0 g) was treated with trifluoroacetic acid (TFA, 6 mL) in DCM (30 mL) at rt for 24 h. After the completion of reaction, the reaction was diluted with toluene (30 mL) and trifluoroacetic acid was removed under anhydrous conditions to yield the amine compound 9 (2.1 g as TFA salt).

The compound 9 (1.0 g, 1 eq.) was then treated with p-aminosulfamoyl-benzoic acid 10 (0.54 g, 1.5 eq.) in the presence of DIC (0.42 mL, 1.5 eq.), HOBt (0.41 g, 1.5 eq.), and Hunig's base (DIEA, 1.3 mL, 4 eq.) in DCM (20 mL) at rt for 72 h. The reaction was concentrated and the residue was purified by silica gel chromatography using 15% acetone in DCM as eluent to afford the desired product 11 as white solid (0.4 g, 36% yield).

The compound 11 (0.4 g, 1 eq.) was reacted with tetrabutylammonium fluoride trihydrate (TBAF, 0.2 g, 1 eq.) in THF (20 mL) at rt for 60 min. The reaction was quenched with aq. ammonium chloride, extracted with ethyl acetate (3×25 mL), the combined organic was dried under sodium sulfate, filtered and concentrated. This residue was purified by silica gel chromatography using 5% acetone in 1:1 hexanes:ethyl acetate to afford (13S,17S)-3-hydroxy-13-methyl-7,8,9,11,12,13,14,15,16,17-decahydro-6H-cyclopenta[a]phenanthren-17-yl 2-(4-sulfamoylbenzamido)acetate (0.15 g, 46% yield) as white solid 6A: $^1$H NMR ($\delta$, DMSO-d$_6$ 300 MHz): 9.15 (t, 1H, —NH, J=5.82 Hz), 8.01 (d, 2H, ArH, J=8.56 Hz), 7.91 (d, 2H, ArH, J=8.54 Hz), 7.50 (bs, 1H, ArOH), 7.02 (d, 1H, ArH, J=8.46 Hz), 6.49 (dd, 1H, ArH, J=2.46, 58.37 Hz), 6.42 (d, 1H, ArH, J=2.42 Hz), 4.67 (t, 1H, 17-CH, J=7.08 Hz), 4.02 (d, 2H, J=5.75 Hz), 0.73 (s, 3H, CH$_3$). IR (cm$^{-1}$): 3369, 3278, 2933, 1736, 1656, 1529. $[\alpha]_D^{23}$=+18° (c=0.5, 1,4-dioxane).

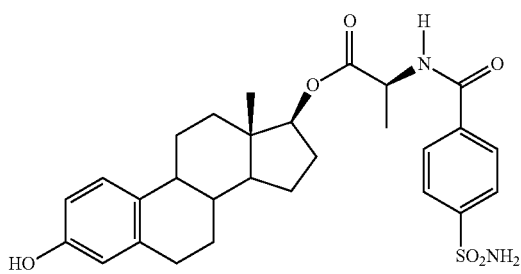 [SMILES: C[C@H](NC(=O)c1ccc(S(N)(=O)=O)cc1)C(=O)O[C@H]1CCC2C3CCc4cc(O)ccc4C3CC[C@@]21C]

(2S)-((13S,17S)-3-hydroxy-13-methyl-7,8,9,11,12,13,14,15,16,17-decahydro-6H-cyclopenta[α]-phenanthren-17-yl) 2-(4-sulfamoylbenzamido)propanoate (12A) was synthesized by following the methods in scheme 5 using similar alanine instead of glycine, as white solid 12A (75 mg): $^1$H NMR ($\delta$, 5:1 CDCl$_3$:DMSO_d$_6$ 300 MHz): 8.54 (s, 1H, ArOH), 8.18 (d, 1H, NH, J=7.03 Hz), 7.99 (dd, 4H, ArH, J=2.4, 8.88 Hz), 7.07 (d, 1H, ArH, J=8.35 Hz), 6.97 (s, 2H, NH$_2$), 6.62 (dd, 1H, ArH, J=2.60, 8.39 Hz), 6.54 (d, 1H, ArH, J=2.46 Hz), 4.77 (t, 1H, 17-CH, J=7.99 Hz), 4.71 (t, 1H, 17-CH, J=7.30 Hz), 1.54 (d, 3H, CH$_3$, J=7.29 Hz), 0.75 (s, 3H, CH$_3$). IR (cm$^{-1}$): 3496, 3381, 2930, 22911, 1743, 1706, 1650. $[\alpha]_D^{23}$=+34° (c=0.5, 1,4-dioxane).

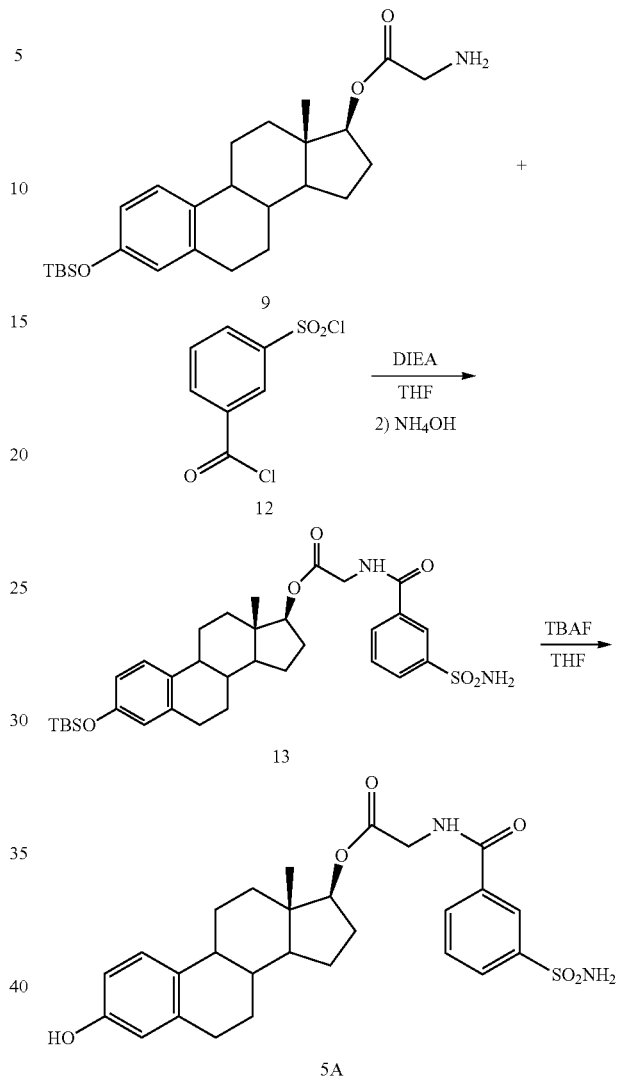

Scheme 6

The steroid 9 (0.7 g) and diisopropylethylamine (DIEA, 1 mL) in THF (20 mL) were chilled to −50° C., followed by the addition of m-chlorosulfonyl-benzoyl chloride 12 (0.9 mL). The resulting yellow mixture was slowly warm to 0° C. over 40 min., and 28% ammonium hydroxide (7 mL) was then added. The resulting mixture was then warmed to rt over 30 min., the reaction was diluted with aq ammonium chloride, extracted with ethyl acetate (3×25 mL), the combined organic was dried under sodium sulfate, filtered and concentrated. This residue was purified by silica gel chromatography using 15% acetone in dichloromethane to afford the white solid 13 (0.53 g, 67% yield).

The compound 13 (0.52 g, 1 eq.) was treated with tetrabutylammonium fluoride trihydrate (TBAF, 0.32 g, 1.2 eq.) in THF (30 mL) at rt for 60 min. The reaction was quenched with aq ammonium chloride, extracted with ethyl acetate (3×25 mL), the combined organic was dried under sodium sulfate, filtered and concentrated. This residue was purified by silica gel chromatography using 5% acetone in 1:1 hexanes:ethyl acetate to afford (13S,17S)-3-hydroxy-13-methyl-7,8,9,11,12,13,14,15,16,17-decahydro-6H-cyclopenta[a]phenanthren-17-yl 2-(3-sulfamoylbenzamido)-acetate (0.31 g, 73% yield) as white solid 5A: ¹H NMR (δ, 5:1 CDCl₃:D₃COD 300 MHz): 8.25 (s, 1H, ArH), 7.96 (d, 2H, ArH, J=7.62 Hz), 7.51 (t, 1H, ArH, J=7.83 Hz), 7.01 (d, 1H, ArH, J=8.43 Hz), 6.52 (d, 1H, ArH, J=8.22 Hz), 6.46 (s, 1H, ArH), 4.68 (t, 1H, 17-CH, J=7.74 Hz), 4.11 (s, 2H, CH₂), 0.75 (s, 3H, CH₃). IR (cm⁻¹): 3416, 3341, 3064, 2934, 2853, 1748, 1642.: [α]$_D^{23}$=+14° (c=0.5, 1,4-dioxane).

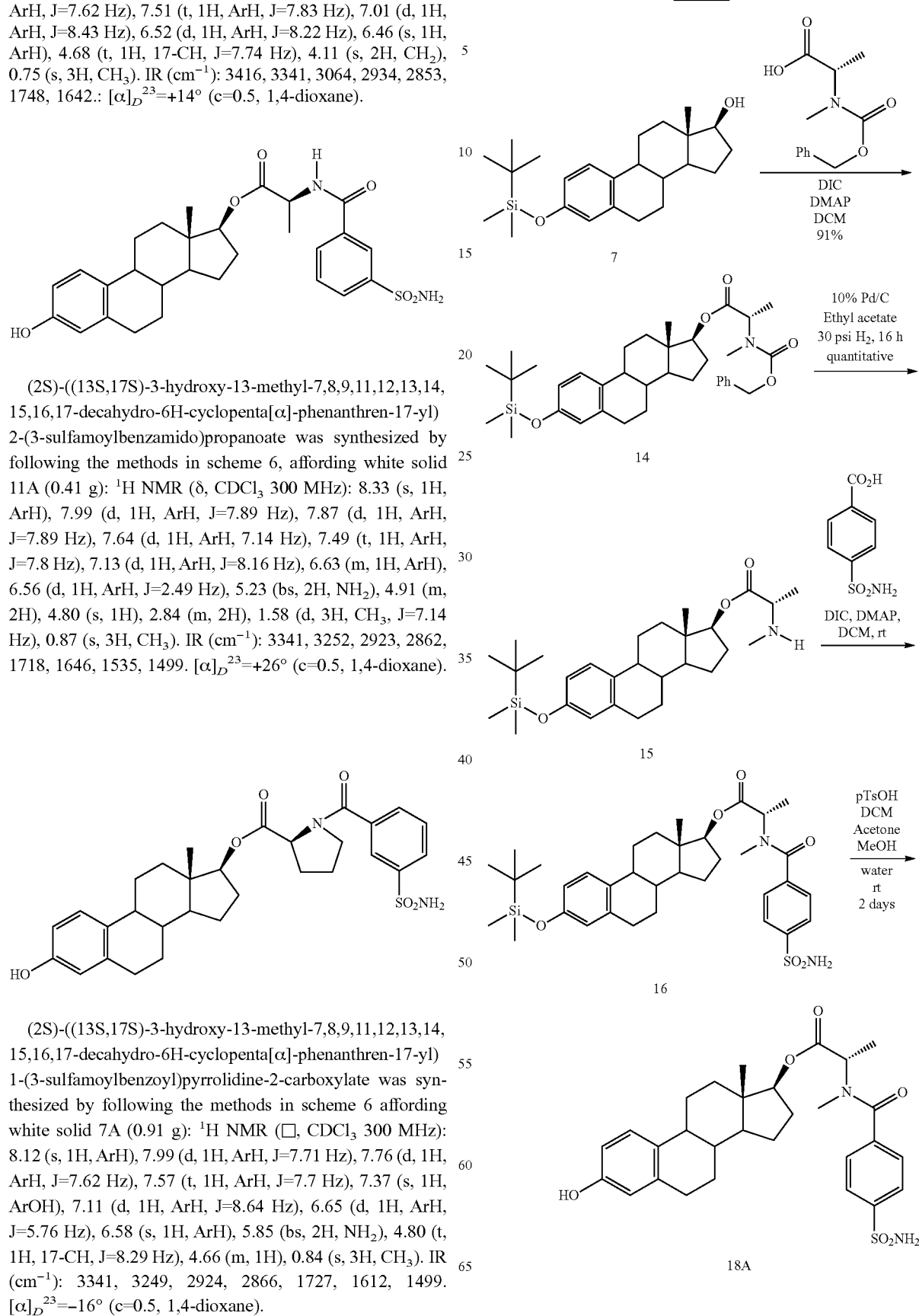

Scheme 7

(2S)-((13S,17S)-3-hydroxy-13-methyl-7,8,9,11,12,13,14,15,16,17-decahydro-6H-cyclopenta[α]-phenanthren-17-yl) 2-(3-sulfamoylbenzamido)propanoate was synthesized by following the methods in scheme 6, affording white solid 11A (0.41 g): ¹H NMR (δ, CDCl₃ 300 MHz): 8.33 (s, 1H, ArH), 7.99 (d, 1H, ArH, J=7.89 Hz), 7.87 (d, 1H, ArH, J=7.89 Hz), 7.64 (d, 1H, ArH, 7.14 Hz), 7.49 (t, 1H, ArH, J=7.8 Hz), 7.13 (d, 1H, ArH, J=8.16 Hz), 6.63 (m, 1H, ArH), 6.56 (d, 1H, ArH, J=2.49 Hz), 5.23 (bs, 2H, NH₂), 4.91 (m, 2H), 4.80 (s, 1H), 2.84 (m, 2H), 1.58 (d, 3H, CH₃, J=7.14 Hz), 0.87 (s, 3H, CH₃). IR (cm⁻¹): 3341, 3252, 2923, 2862, 1718, 1646, 1535, 1499. [α]$_D^{23}$=+26° (c=0.5, 1,4-dioxane).

(2S)-((13S,17S)-3-hydroxy-13-methyl-7,8,9,11,12,13,14,15,16,17-decahydro-6H-cyclopenta[α]-phenanthren-17-yl) 1-(3-sulfamoylbenzoyl)pyrrolidine-2-carboxylate was synthesized by following the methods in scheme 6 affording white solid 7A (0.91 g): ¹H NMR (□, CDCl₃ 300 MHz): 8.12 (s, 1H, ArH), 7.99 (d, 1H, ArH, J=7.71 Hz), 7.76 (d, 1H, ArH, J=7.62 Hz), 7.57 (t, 1H, ArH, J=7.7 Hz), 7.37 (s, 1H, ArOH), 7.11 (d, 1H, ArH, J=8.64 Hz), 6.65 (d, 1H, ArH, J=5.76 Hz), 6.58 (s, 1H, ArH), 5.85 (bs, 2H, NH₂), 4.80 (t, 1H, 17-CH, J=8.29 Hz), 4.66 (m, 1H), 0.84 (s, 3H, CH₃). IR (cm⁻¹): 3341, 3249, 2924, 2866, 1727, 1612, 1499. [α]$_D^{23}$=−16° (c=0.5, 1,4-dioxane).

N-Cbz-Methylalanine (2.45 g, 2 eq.) was treated with DIC (1.6 mL, 2 eq.) in DCM (33 mL) for 30 min under nitrogen at rt. TBS-Estradiol 7 (2.0 g, 1 eq.) and DMAP (0.063 g, 0.1 eq.) were then added and the resulting white mixture was stirred for 16 h rt. After filtration, the filtrate was concentrated and the residue was purified by silica gel chromatography using 5-40 ethyl acetate in hexanes as eluent to afford the white solid product 14 (2.85 g, 91% yield).

The Cbz group of ester 14 (2.85 g) was then removed using Pd/C (10% Pd, 0.51 g) and hydrogen (30 psi) on a Pan shaker in ethyl acetate (35 mL) as solvent for 16 h. After filtration through celite and concentration of the solvent, the white solid product 15 (2.2 g, quantitative) was obtained.

The amide formation of the amine 15 was carried out using p-sulfamoylbenzoic acid (2.22 g, 2.4 eq.) and DIC (1.7 mL, 2.4 eq.) in DCM (75 mL) followed by the addition of the amine 15 (2.2 g, 1 eq.) and DMAP (56 mg, 0.1 eq.). The reaction was not soluble initially so ethyl acetate (35 mL) was added and the reaction mixture was stirred at rt for 3 days. The reaction was filtered and the filtrate was concentrated. The residue was purified by silica gel chromatography using 10% ethyl acetate in hexanes as eluent to afford the white solid product 16 (1.90 g, 63% yield).

The silyl ether 16 (1.90 g) was then removed using p-toluenesulfonic acid (1.16 g, 2 eq.) in DCM (14 mL), acetone (14 mL), methanol (0.4 mL) and water (0.3 mL) at rt for 16 h. The reaction was quenched with aq. sodium bicarbonate and extracted with ethyl acetate (2×60 mL). The combined organic layer was dried with sodium sulfate, filtered and concentrated. The residue was purified by silica gel chromatography using 10-30% acetone in DCM as eluent to afford [(13S,17S)-3-hydroxy-13-methyl-6,7,8,9,11,12,14,15,16,17-decahydrocyclopenta[a]phenanthren-17-yl](2S)-2-[methyl-(4-sulfamoylbenzoyl)amino]propanoate as the white solid 18A (1.47 g, 94% yield): $^1$H NMR (δ, CDCl$_3$ 300 MHz): 7.96 (d, 2H, J=8.1 Hz), 7.99 (d, 2H, J=8.1 Hz), 7.13 (d, 1H, ArH, J=8.1 Hz), 6.62 (dd, 1H, ArH, J=2.7, 8.4 Hz), 6.54 (d, 1H, ArH, J=2.7 Hz), 5.30 (s, 1H), 4.95 (s, 2H, NH$_2$), 4.80 (m, 1H), 3.00 (s, 1H, CH$_3$, rotamer), 2.90 (s, 2H, CH$_3$, rotamer), 0.85 (s, 2H, CH$_3$, rotamer), 0.83 (s, 1H, CH$_3$, rotamer). IR (cm$^{-1}$): 3353, 3257, 2924, 2862, 1731, 1617. $[α]_D^{24}$=−10° (c=0.5, 1,4-dioxane).

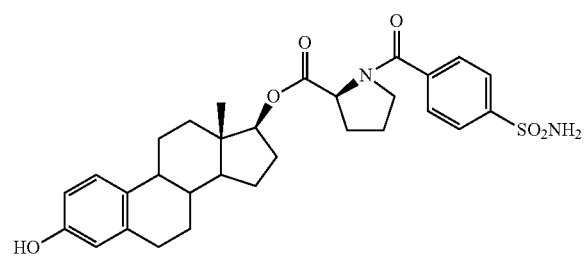 [SMILES: C[C@]12CCC3c4ccc(O)cc4CCC3C1CC[C@@H]2OC(=O)[C@@H]1CCCN1C(=O)c1ccc(S(N)(=O)=O)cc1]

(2S)-((13S,17S)-3-hydroxy-13-methyl-7,8,9,11,12,13,14,15,16,17-decahydro-6H-cyclopenta[a]-phenanthren-17-yl) 1-(4-sulfamoylbenzoyl)pyrrolidine-2-carboxylate was synthesized by following the methods in scheme 7 affording white solid 8A (0.51 g): $^1$H NMR (δ, CDCl$_3$ 300 MHz): 7.96 (d, 2H, ArH, J=7.25 Hz), 7.66 (d, 1.6H rotamer, ArH, J=7.28 Hz), 7.47 (d, 0.4H rotamer, ArH, J=7.28 Hz), 7.40 (s, 1H, ArOH), 7.10 (d, 1H, ArH, J=8.43 Hz), 6.64 (d, 1H, ArH, J=8.31 Hz), 6.58 (s, 1H, ArH), 6.04 (bs, 2H, NH$_2$), 4.81 (t, 1H, 17-CH), 4.67 (m, 1H, CH), 0.84 (s, 3H, CH$_3$). IR (cm$^{-1}$): 3378, 3218, 2925, 1738, 1615, 1498. $[α]_D^{23}$=−12° (c=0.5, 1,4-dioxane).

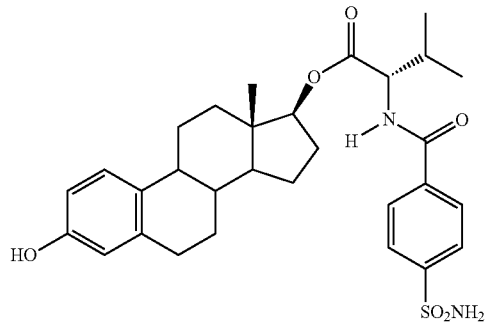 [SMILES: CC(C)[C@H](NC(=O)c1ccc(S(N)(=O)=O)cc1)C(=O)O[C@H]1CCC2C3CCc4cc(O)ccc4C3CC[C@@]21C]

[(13S,17S)-3-hydroxy-13-methyl-6,7,8,9,11,12,14,15,16,17-decahydrocyclopenta[a]phenanthren-17-yl] (2S)-3-methyl-2-[(4-sulfamoylbenzoyl)amino]butanoate was synthesized by following the methods in scheme 7 affording white solid 19A (1.90 g): $^1$H NMR (δ, 5 CDCl$_3$ 300 MHz): 7.97 (d, 2H, ArH, J=8.7 Hz), 7.91 (d, 2H, ArH, J=8.4 Hz), 7.13 (d, 1H, ArH, J=8.1 Hz), 6.81 (d, 1H, J=8.4 Hz), 6.63 (dd, 1H, ArH, J=2.7, 8.4 Hz), 6.56 (d, 1H, ArH, J=2.1 Hz), 5.01 (s, 2H, NH$_2$), 4.79 (m, 3H), 1.04 (dd, 6H, J=2.7, 6.9 Hz), 0.87 (s, 3H, CH$_3$). IR (cm$^{-1}$): 3338, 3252, 2967, 2924, 1722, 1710, 1657. $[α]_D^{24}$=+40° (c=0.6, 1,4-dioxane).

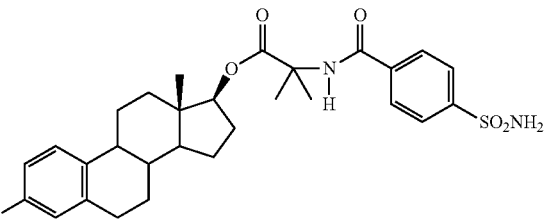

[(13S,17S)-3-hydroxy-13-methyl-6,7,8,9,11,12,14,15,16,17-decahydrocyclopenta[a]phenanthren-17-yl] 2-methyl-2-[(4-sulfamoylbenzoyl)amino]propanoate was synthesized by following the methods in scheme 7 affording white solid 20A (0.61 g): $^1$H NMR (δ, DMSO-d$_6$ 300 MHz): 8.98 (s, 1H), 8.78 (s, 1H), 7.97 (d, 2H, ArH, J=8.4 Hz), 7.89 (d, 2H, ArH, J=8.1 Hz), 7.48 (s, 2H, NH$_2$), 7.02 (d, 1H, ArH, J=8.7 Hz), 6.48 (dd, 1H, ArH, 2.4, 8.1 Hz), 6.41 (d, 1H, ArH, J=2.1 Hz), 4.55 (t, 1H, J=8.4 Hz), 1.47 (s, 6H, di-CH$_3$), 0.66 (s, 3H, CH$_3$). IR (cm$^{-1}$): 3504, 3355, 3168, 3067, 2922, 2867, 1727, 1648. $[α]_D^{24}$=+48° (c=0.5, 1,4-dioxane).

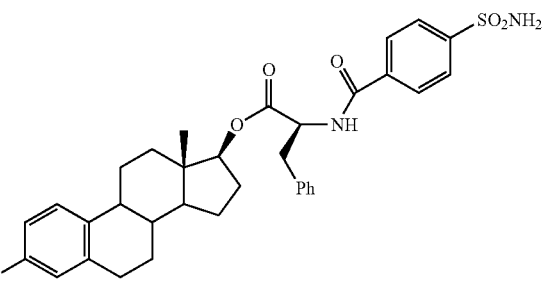

[(13S,17S)-3-hydroxy-13-methyl-6,7,8,9,11,12,14,15,16,17-decahydrocyclopenta[a]phenanthren-17-yl] (2S)-3-phenyl-2-[(4-sulfamoylbenzoyl)amino]propanoate was synthesized by following the methods in scheme 7 as white solid 21A (0.44 g): $^1$H NMR (δ, DMSO-$d_6$ 300 MHz): 9.04 (d, 1H, NH, J=7.5 Hz), 9.00 (s, 1H, OH), 7.94 (d, 2H, ArH, J=8.4 Hz), 7.89 (d, 2H, ArH, J=8.1 Hz), 7.49 (s, 2H, NH$_2$), 7.30 (m, 5H), 7.02 (d, 1H, ArH, J=8.4 Hz), 6.49 (dd, 1H, ArH, J=1.8, 8.1 Hz), 6.42 (d, 1H, ArH, J=1.8 Hz), 4.67 (m, 2H), 0.68 (s, 3H, CH$_3$). IR (cm$^{-1}$): 3351, 2924, 2868, 1722, 1650. $[\alpha]_D^{24}$=+42° (c=0.5, 1,4-dioxane).

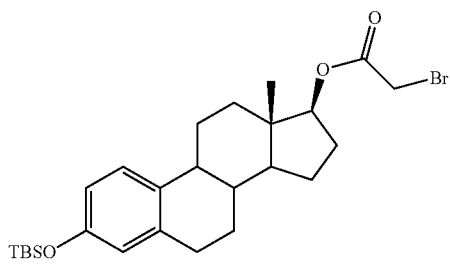 [SMILES: CC(C)(C)[Si](C)(C)Oc1ccc2c(c1)CCC1C2CC[C@@]2(C)C1CC[C@@H]2OC(=O)CBr]

Preparation of intermediate 17-(13S,17S)-3-(tert-butyldimethylsilyloxy)-13-methyl-7,8,9,11,12,13,14,15,16,17-decahydro-6H-cyclopenta[a]phenanthren-17-yl 2-bromoacetate: A round bottom flask was charged with 7 (2.0 g, 5.3 mmol) and dissolved in 5 mL of DCM and 2 mL (25 mmol) of pyridine. The mixture was chilled to −78° C. Bromoacetyl chloride (1 mL, 6.3 mmol) was then dissolved in 10 mL of DCM and then added to the steroid solution dropwise. At the end of the addition, the mixture was removed from the bath and allowed to warm to room temperature. After thirty minutes of having been removed from the ice bath, TLC (1:4 EtOAc:hexanes) indicated complete conversion of starting material. The mixture was treated with ice-cold 2 M HCl (50 mL), and the layers were then separated. The organic layer was washed with water (2×50 mL), brine, and then dried over sodium sulfate. The product was isolated using flash chromatography (5% EtOAc in hexanes) to afford 1.32 g of material 17 (49%). $^1$H NMR (δ, CDCl$_3$, 300 MHz): 7.09 (d, 1H, J=4.3 Hz), 6.50 (d, 1H, J=3.9 Hz), 6.43 (s, 1H), 4.69 (t, J=8.5 Hz, 1H), 4.08 (s, 2H), 0.98 (s, 9H), 0.85 (s, 3H,), 0.19 (s, 6H).

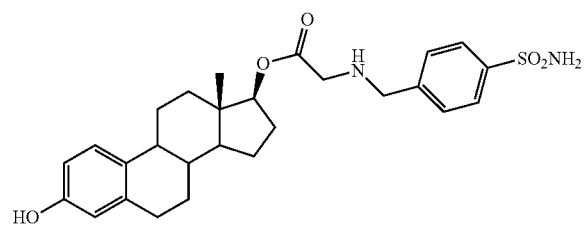

Preparation of (13S,17S)-3-hydroxy-13-methyl-7,8,9,11,12,13,14,15,16,17-decahydro-6H-cyclopenta-[a]phenanthren-17-yl)-2-(4-sulfamoylbenzylamino)-acetate 26A: 500 mg (2.3 mmol) of 4-homosulfanilamide hydrochloride was dissolved in 5 mL DMF and 1 equivalent of potassium carbonate was added followed by addition of 0.5 equivalents of Hunig's base at room temperature and a crystal of tertbutylammonium iodine. After a period of 20 min to the solution was directly added 1 equivalent of estradiol-bromo acetate ester 17 and then the reaction was allowed to stir for 12 hours at room temperature. The crude mixture was then filtered and directly loaded onto a silica column and separated using MPLC to afford 75 mg of the desired intermediate, which was then subjected to desilyation conditions described. $^1$H NMR (δ, CDCl$_3$, 300 MHz): 7.77-7.74 (d, 2H, J=8.4 Hz), 7.51-7.48 (d, 2H, J=8.4 Hz), 7.04-7.02 (d, 1H), 6.51-6.48 (d, 1H), 6.43-6.42 (s, 1H, J=2.4 Hz), 5.45 (s, 1H,), 4.67 (t, J=8.9 Hz, 1H), 4.22-4.06 (m, 2H), 3.99 (s, 2H), 3.80 (s, 2H), 0.73 (s, 3H). IR (cm$^{-1}$): 3419, 3311, 2920, 2832, 1739, 1499, 1221, 1152, 1127, 1039, 750. Optical Rotation: $[\alpha]_D^{20}$=+42° (C=0.5, MeOH]). MP: 201-205° C.

General procedure for TBS group removal—the silyl ether is dissolved in THF (generally, the concentration is kept around 0.1 M) and one equivalent of TBAF (1.0 M in THF) is added. Complete, clean desilylation is observed by one hour. The mixture is then treated with ammonium chloride solution, and extracted.

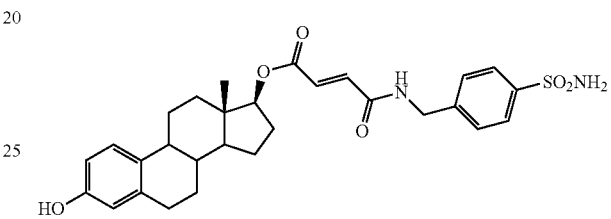

Preparation of (13S,17S)-3-hydroxy-13-methyl-7,8,9,11,12,13,14,15,16,17-decahydro-6H-cyclopenta[a]phenanthren-17-yl)-4-oxo-4-(4-sulfamoylbenzylamino)-but-2-enoate 4A: A round bottom flask was charged with mono-ethyl fumerate (2.34 g, 16.3 mmol) which was then dissolved in DMF (10 mL). HOBt (2.75 g, 17.9 mmol) was added and then after 5 minutes DCC (4.02 g, 19.5 mmol) was added. The mixture was allowed to stir for twenty minutes before addition of 4-homosulfanilamide HCl (3.95 g, 17.8 mmol) and finally Hunig's base. After 12 hrs the reaction was judged complete by TLC and then purified by MPLC using a 10 to 30% acetone gradient in DCM, to afford 1.2 g of the desired intermediate. This was then subjected to saponification using a 20% NaOH solution for 1 h at 80° C., followed by treatment with 50% HCl to afford the free acid as a white crystalline powder. The free acid (0.30 g, 1.06 mmol) was dissolved in pyridine (3 mL, 37 mmol), followed by addition of 3-TBS-estradiol (0.30 g, 0.78 mmol), 0.4 g of DCC (1.94 mmol), and 25 mg (0.13 mmol) of p-TSA. The mixture was allowed to stir at room temperature for 72 hours, at which time it was judged complete by TLC. The mixture was diluted with 2 mL of water, 3 mL of 10% HCl and 25 mL of ethyl acetate. The mixture was filtered and the organic layer was separated. The organic solution was washed with saturated solutions of NaHCO$_3$ and finally NaCl. The solution was dried over magnesium sulfate, filtered and the solvent evaporated obtaining a crude product 18 which was purified on silica gel with a gradient of acetone in DCM from 5-20% to afford the desired intermediate in 45% yield. This material was then subjected to the general desilyation conditions described in 26A. $^1$H NMR CDCl$_3$, 300 MHz): 7.81-7.78 (d, 2H, J=8.4 Hz), 7.37-7.35 (d, 2H, J=8.4 Hz), 7.04-7.02 (d, 1H), 6.90-6.83 (q, 2H), 6.52-6.49 (d, 1H), 6.48 (s, 1H), 5.92 (s, 1H), 4.81 (t, J=8.9 Hz, 1H), 4.42 (s, 2H), 1.98-1.92 (m 4H), 0.73 (s, 3H). IR (cm$^{-1}$): 3331, 2920, 2839, 1705, 1658, 1221, 1152, 1127, 1039, 750. Optical Rotation: $[\alpha]_D^{20}$=+66° (C=0.5, MeOH]). MP: 177-180° C.

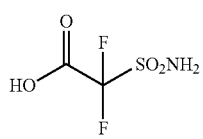

2,2-difluoro-2-sulfamoylacetic acid 19 was synthesized as described by Boyle, et al, Organic Biomolecular Chemistry, 2005, 3, 222-224.

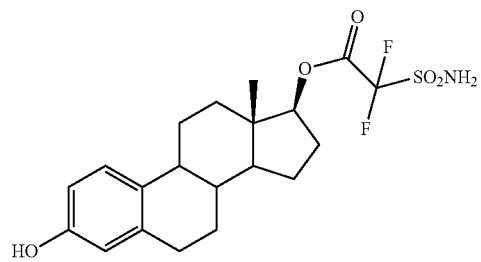 [SMILES: C[C@]12CCC3c4ccc(O)cc4CCC3C1CC[C@@H]2OC(=O)C(F)(F)S(N)(=O)=O]

(13S,17S)-3-hydroxy-13-methyl-7,8,9,11,12,13,14,15,16,17-decahydro-6H-cyclopenta[a]phenanthren-17-yl-2,2-difluoro-2-sulfamoylacetate 9A: Intermediate 19 (0.35 g, 2.0 mmol) was placed in an oven-dried round bottom flask, and 3.65 mL of $POCl_3$ (40.0 mmol) was added. An oven-dried condenser was placed atop the flask, and the mixture was allowed to reflux for five hours, after which time excess $POCl_3$ was removed under vacuum (required both rotovap and 24 h high vacuum). A crystalline solid was resultant (0.376 g, 97% yield). 7 (0.39 g, 1.05 mmol) was dissolved in 2 mL DCM and 0.4 mL pyridine (5 mmol), and chilled to −78° C. The acid chloride of 19 was dissolved in 3 mL DCM, and added to the steroid solution. The mixture was allowed to stir for ten minutes before removal from the bath and gradual warming to room temperature. After one hour at room temperature, the reaction was judged complete, and all volatiles were removed under vacuum. The crude mixture was purified by flash chromatography, using 15% ethyl acetate in hexanes, affording 353 mg of the desired intermediate (65% yield). The intermediate was then desilyated in the usual manner, and purified using flash chromatography using 10% acetone in DCM, affording 236 mg of analog 9A (96% yield): $^1$H NMR (300 MHz, DMSO-$d_6$) δ ppm 9.01 (s, 1H), 8.94 (bs, 2H), 7.04 (d, J=10.6 Hz, 1H), 6.51 (d, J=8.4 Hz, 1H), 6.43 (s, 1H), 4.87 (t, J=7.93 Hz, 1H), 0.75 (s, 3H); IR (cm$^{-1}$) 3378, 3358, 2921, 2854, 1767, 1494, 1355, 1154; Optical Rotation: $[α]_D^{20}$=+38 (MeOH); MP: 209.5-212.0° C.

famoylacetate 10A: A round bottom flask was charged with chlorosulfonylacetyl chloride (0.50 g, 2.8 mmol) and dissolved in 2 mL DCM. The mixture was chilled to 0° C. A solution of 7 (546 mg, 1.4 mmol) in 3 mL DCM was then added dropwise. TLC after 1 hour at this temperature indicated incomplete conversion of starting material, so the mixture was then allowed to warm up to room temperature. 3.5 hours of stirring at room temperature was required for full acylation of the 17-alcohol of the steroid. Once this had occurred, 2 mL of 28% ammonium hydroxide was added dropwise. After ten minutes, TLC profile was completely different than that of an aliquot of the mixture that had been removed immediately prior to ammonia addition. All volatiles were then removed under vacuum, rendering 1.12 g of crude material, which was then subjected to flash chromatography using 5% acetone in DCM. This produced 0.16 g of the desired intermediate (23% yield). The material was then desilyated in the usual manner to give the final analog 10A: $^1$H NMR (δ, DMSO-$d_6$, 300 MHz): 9.01 (s, 1H), 7.18 (s, 2H), 7.04 (d, J=8.60 Hz, 1H), 6.50 (d, J=7.94 Hz, 1H,), 6.43 (s, 1H), 4.70 (t, J=8.58 Hz, 1H), 4.10 (s, 2H) 0.801 (s, 3H). IR (cm$^{-1}$): 3429, 3353, 3303, 2925, 2854, 1725, 1607, 1502, 1448, 1347, 1318. Optical Rotation: $[α]_D^{20}$=+47 (MeOH); MP: 218-220° C.

Note—if pyridine is used as a proton sponge in this conversion (as is generally the case with acylation by acid chlorides) no regioselectivity is observed, resulting in the 17-alcohol displacing both the acid and sulfonyl chlorides. This was observed at different temperatures and solvents.

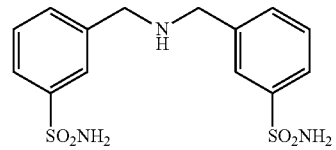

Synthesis of 3,3'-azanediylbis(methylene)dibenzenesulfonamide 20: 3-cyanobenzenesulfonamide (1.0 g, 5.49 mmol) was placed in a hydrogenation jar along with 0.6 g of 10% w/w palladium on activated charcoal. 10 mL of MeOH was added and the mixture was subjected to hydrogenation conditions (20 psi) using a Pan shaker. The mixture was shaken overnight and the next day, TLC (30% acetone in DCM) indicated complete conversion of starting material. The mixture was filtered through Celite, and the cake washed with methanol to afford the material as a white solid (0.78 g, 87%). $^1$H NMR (300 MHz, δ, DMSO-$d_6$) 7.84 (s, 2H), 7.70 (d, J=7.43 Hz, 2H), 7.59-7.49 (m, 4H), 7.32 (s, 4H), 3.77 (s, 4H), 2.90 (bs, 1H).

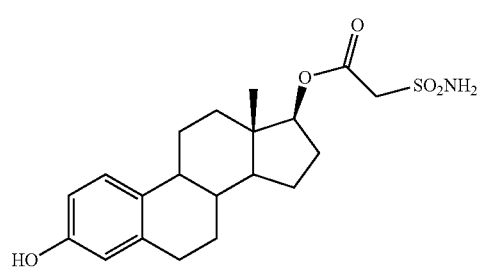 [SMILES: C[C@]12CCC3c4ccc(O)cc4CCC3C1CC[C@@H]2OC(=O)CS(N)(=O)=O]

(13S,17S)-3-hydroxy-13-methyl-7,8,9,11,12,13,14,15,16,17-decahydro-6H-cyclopenta[a]phenanthren-17-yl 2-sul-

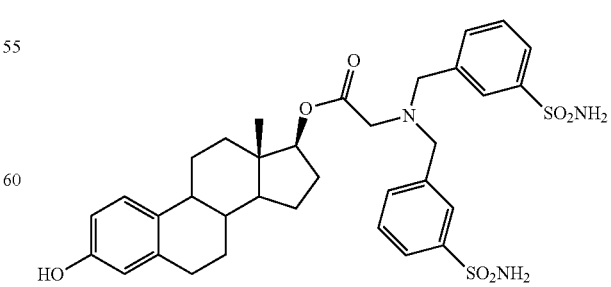

(13S,17S)-3-hydroxy-13-methyl-7,8,9,11,12,13,14,15,16,17-decahydro-6H-cyclopenta[a]phenanthren-17-yl 2-(bis (3-sulfamoylbenzyl)amino)acetate 13A: A round bottom flask was charged with intermediate 20 (0.26 g, 0.51 mmol), and dissolved in DMF (5 mL). Potassium carbonate was added (0.14 g, 1.01 mmol), then intermediate 17 (0.18 g, 0.51 mmol) and finally a few crystals of TBAI. The mixture was allowed to stir overnight. The following day, the reaction was judged complete by TLC, and the mixture was added straight to a silica gel column and isolated using a 50 to 70% ethyl acetate gradient in hexanes. The purified intermediate was then subjected to the aforementioned desilylation protocol to afford the analog 13A; $^1$H NMR (300 MHz, CDCl$_3$) δ ppm 8.20 (s, 2H), 7.82-7.79 (m, 2H), 7.45-7.43 (m, 4H), 7.14 (d, J=4.34 Hz, 1H), 6.64 (d, J=7.14 Hz, 1H), 6.57 (s, 1H), 5.49 (s, 4H), 4.78 (t, J=9.00 Hz, 1H), 4.65 (s, 1H), 3.88 (s, 4H), 3.47 (s, 2H), 0.84 (s, 3H); IR (cm$^{-1}$) 3357, 3257, 2925, 1712, 1326, 1150; ESI-MS 668.1 (M+H)$^+$; Optical Rotation: $[\alpha]_D^{20}$=+32 (MeOH).

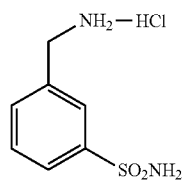 [SMILES: NS(=O)(=O)c1cccc(CNCl)c1]

Synthesis of 3-(aminomethyl)benzenesulfonamide HCl 21: A 2-necked round bottom flask was charged with 3-cyanobenzenesulfomamide (1.5 g, 8.23 mmol) and 0.80 g of palladium on activated charcoal (10% w/w). 30 mL of MeOH and 5 mL of 2M HCl was added. One port was charged with a septa and the other was equipped with a flow adaptor with a stopcock. The contents of the flask were evacuated and then re-filled with nitrogen. This was repeated twice, and after a final evacuation a balloon filled with hydrogen was introduced through the septa, and the flask was charged with hydrogen. The balloon was removed and the flask evacuated. This was repeated twice and after the final evacuation the balloon was replaced. The mixture was allowed to stir until TLC indicted complete conversion of starting material (required 4 hours). The mixture was then filtered through Celite, and the volatiles removed under vacuum, leaving 3.2 g of a crystalline semi-solid. This was tritiated with ethyl acetate, leaving 1.5 g of an off-white solid 21 (83%); $^1$H NMR (300 MHz, DMSO-d$_6$) δ ppm 7.96 (s, 1H), 7.84 (d, J=7.07 Hz, 1H), 7.76 (d, J=7.06 Hz, 1H), 7.63 (d, J=7.73 Hz, 1H), 7.46 (s, 2H), 4.09 (s, 2H); LCMS-ESI, 170.0 (free base, M-NH$_2$+H)$^+$, 187.1 (free base, M+H)$^+$.

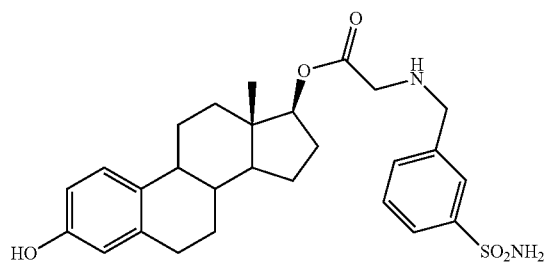 [SMILES: C[C@]12CCC3c4ccc(O)cc4CCC3C1CC[C@@H]2OC(=O)CNCc1cccc(S(N)(=O)=O)c1]

Synthesis of (13S,17S)-3-hydroxy-13-methyl-7,8,9,11,12,13,14,15,16,17-decahydro-6H-cyclopenta[a]phenanthren-17-yl 2-(3-sulfamoylbenzylamino)acetate 14A: A round bottom flask was charged with 3-TBS-estradiol (0.60 g, 1.2 mmol), intermediate 21 (0.40 g, 1.8 mmol), 18-crown-6 ether (16.0 mg, 0.06 mmol), TBAI (44.0 mg, 0.12 mmol), potassium carbonate (0.83 g, 6.0 mmol), and 5 mL DMF. The reaction was allowed to stir under nitrogen for 48 hours, at which time the steroidal starting material was completely consumed as observed by TLC (1:3 EtOAc:hexanes). The mixture was diluted with water, forming a precipitate, which was then collected by vacuum filtration. The cake was washed with water (50 mL), and then dried under vacuum. 668 mg of crude material was collected, which was then subjected to flash chromatography using 10% acetone in DCM to afford 217 mg of the desired intermediate (30% yield). The intermediate was then subjected to the aforementioned desilylation protocol, and after chromatography using a 15 to 50% gradient of acetone in DCM, 140 mg of product 14A was collected (96% yield); $^1$H NMR (δ, DMSO-d$_6$, 300 MHz): 9.00 (s, 1H), 7.81 (s, 1H), 7.71-7.68 (m, 1H), 7.52-7.50 (m, 2H), 7.33 (s, 2H), 7.04 (d, J=9.00 Hz, 1H), 6.502 (d, J=7.80 Hz 1H), 6.427 (s, 1H), 4.68 (t, J=8.04 Hz, 1H), 3.803 (s, 2H), 0.772 (s, 3H, —CH$_3$); IR (cm$^{-1}$): 3412, 3294, 2917, 1721, 1305, 1234, 1146; Optical Rotation: $[\alpha]_D^{20}$=+32 (MeOH); MP: 193.0-195.2° C.

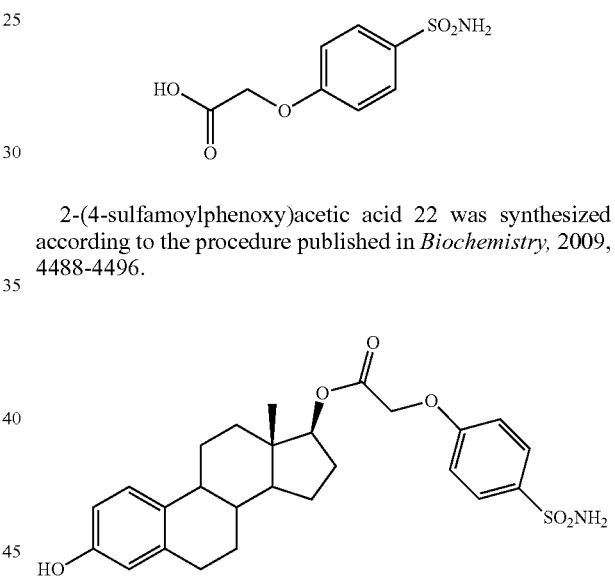

2-(4-sulfamoylphenoxy)acetic acid 22 was synthesized according to the procedure published in *Biochemistry*, 2009, 4488-4496.

(13S,17S)-3-hydroxy-13-methyl-7,8,9,11,12,13,14,15,16,17-decahydro-6H-cyclopenta[a]phenanthren-17-yl 2-(4-sulfamoylphenoxy)acetate 15A: A round bottom flask was charged with 22 (0.50 g, 2.16 mmol) and dissolved in 5 mL DMF. Hunig's base was added (0.5 mL, 2.9 mmol) and then DIC (0.7 mL, 4.32 mmol). This mixture was allowed to stir for thirty minutes before the addition of 3-TBS-estradiol 7 (558 mg, 1.44 mmol), and then DMAP (88 mg, 0.72 mmol). The mixture was allowed to stir for 48 hours, after which time the mixture was diluted with 2M HCl (50 mL), and then extracted with diethyl ether. The combined organic layers were then washed with water, brine, and then dried over sodium sulfate. The desired intermediate was then isolated by flash chromatography, using a 2 to 10% gradient of acetone in DCM, obtaining 110 mg (13% yield). It was then subjected to desilylation in the usual manner, affording 81 mg of analog 15A (93% yield): $^1$H NMR (δ, DMSO-d$_6$, 300 MHz): 9.00 (s, 1H), 7.81 (s, 1H), 7.71-7.68 (m, 1H), 7.52-7.50 (m, 2H), 7.33 (s, 2H), 7.04 (d, J=9.00 Hz, 1H), 6.50 (d, J=7.80 Hz, 1H), 6.43 (s, 1H), 4.68 (t, J=8.04 Hz, 1H), 3.80 (s, 2H), 0.77 (s, 3H,). IR (cm$^{-1}$): 3362, 3257, 2917, 2862, 1733, 1595, 1498, 1209, 1154, 831, 671. Optical Rotation: $[\alpha]_D^{20}$=+30 (MeOH).

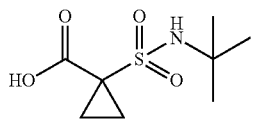

Synthesis of 1-(N-tert-butylsulfamoyl)cyclopropanecarboxylic acid 23: N-t-butyl-1-cyclopropylsulfonamide was made as described in *Synlett*, 2006, 725-728. This starting material (0.78 g, 4.4 mmol) was dissolved in 15 mL anhydrous THF, and chilled to −78° C. under nitrogen. A 2.5M solution of n-butyl lithium in hexanes (3.7 mL, 9.2 mmol) was added to the mixture, and allowed to warm to room temperature with stirring over 2 hours. A filter flask was charged with dry ice. The flask was sealed with a stopper, and to the inlet a hose was attached which was connected to a drying tube filled with calcium sulfate, in line with a cold trap immersed in dry-ice-acetone and finally a large bore needle. Water was then added to the filter flask, and the stopper replaced, and the mixture was saturated with carbon dioxide (a vent needle was introduced to the reaction pot through septa) for 2 hours. 10 mL of 2M HCl was then added, and the aqueous was extracted with DCM (3×25 mL). The combined organic layers were washed with brine, and dried with sodium sulfate. The solvent was removed in vacuo, affording 0.81 g (83% yield) of the desired intermediate 23 as a pale yellow solid: $^1$H NMR (300 MHz, CDCl$_3$) δ ppm 5.05 (bs, 1H), 1.92-1.85 (m, 2H), 1.83-1.76 (m, 2H), 1.37 (s, 9H). IR (cm$^{-1}$): 3320, 2984, 1691, 1322, 1301, 1131, 1003.

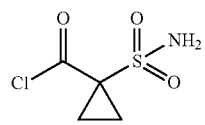

Synthesis of 1-sulfamoylcyclopropanecarbonyl chloride 24: A round bottom flask was charged with acid 23 (0.50 g, 2.3 mmol) and suspended in DCM (2 mL) and TFA (2 mL, 23 mmol). The mixture was allowed to stir under nitrogen overnight. The next day, precipitates had formed, which was collected by vacuum filtration and washed with ice-cold 1:1 DCM:hexanes, affording 185 mg of the pure deprotected sulfonamide (49% yield). The volatiles from the mother liquor were removed, rendering a solid which was identified as the deprotected sulfonamide, in approximately 65% purity (the other impurity was unreacted N-t-butyl-1-cyclopropylsulfonamide from the previous step). The pure material was then placed in a round bottom flask equipped with a stir bar. Thionyl chloride was added (2 mL, 27.6 mmol) and a condenser was placed atop, and the flask was then placed in a pre-heated oil bath. The mixture was allowed to reflux, and required about twenty minutes to completely dissolve. An aliquot was removed from the mixture and all volatiles removed under vacuum. It was observed by IR analysis the carbonyl shift relative to the acid had completely disappeared, and a new carbonyl shift was present. In subsequent attempts, it was determined that when all the material had dissolved in refluxing thionyl chloride, the reaction was complete. However, with some batches of starting material, if complete solution had not been achieved by thirty minutes, about 5-10 μL of DMF was enough to complete the conversion within minutes. In this described attempt, 201 mg of yellow crystalline solid 24 was resultant upon removal of thionyl chloride in vacuo: $^1$H NMR (300 MHz, CDCl$_3$) δ ppm 5.05 (bs, 2H), 2.06 (bs, 4H). IR (cm$^{-1}$) 3387, 3265, 1771, 1532, 1330.

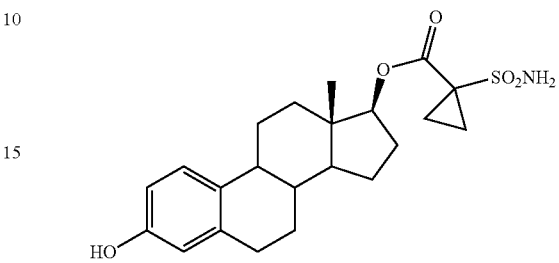

(13S,17S)-3-hydroxy-13-methyl-7,8,9,11,12,13,14,15,16,17-decahydro-6H-cyclopenta[a]phenanthren-17-yl 1-sulfamoylcyclopropanecarboxylate 16A: A septa-capped vial was charged with 3-TBS-estradiol 7 (222 mg, 0.57 mmol), and DMAP (7.0 mg, 0.057 mmol), and dissolved in 2 mL DCM and 0.23 mL pyridine (2.85 mmol). Intermediate 24 (315 mg, 1.72 mmol) was suspended in 3 mL DCM and added to the steroid solution as a slurry. The cap was replaced, a nitrogen line was introduced, and the mixture was allowed to stir overnight. The next day, HPLC analysis indicated about 70% conversion of starting material. The mixture was rotovaped onto silica gel and subjected to flash chromatography, using a 20 to 50% ethyl acetate in hexanes gradient, affording 136 mg of the desired intermediate (45% yield). The material was desilyated in the usual manner to afford 16A: $^1$H NMR (δ, DMSO-d$_5$, 300 MHz): 9.00 (s, 1H), 7.04 (d, J=8.44 Hz, 1H), 6.96 (s, 2H), 6.50 (dd, J=8.24 Hz, 2.12 Hz, 1H), 6.43 (d, J=2.42 Hz, 1H) 4.67 (t, J=8.73 Hz, 1H), 0.789 (s, 3H). IR (cm$^{-1}$): 3408, 3353, 3273, 2934, 1715, 1611, 1498, 1326, 1138. ESI-MS −437.1 (M+H$_2$O)$^+$, 861.3 (2M+Na)$^+$; 418.1 (M−1)$^-$. Optical Rotation: $[\alpha]_D^{20}$=+42 (MeOH); MP: 225-227° C.

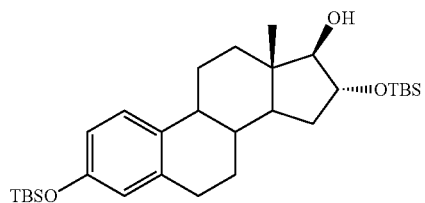 [SMILES: CC(C)(C)[Si](C)(C)Oc1ccc2c(c1)CCC1C2CC[C@@]2(C)C1C[C@@H](O[Si](C)(C)C(C)(C)C)[C@@H]2O]

Synthesis of (13S,16R,17R)-3,16-bis(tert-butyldimethylsilyloxy)-13-methyl-7,8,9,11,12,13,14,15,16,17-decahydro-6H-cyclopenta[a]phenanthren-17-ol 25: A 2-liter 3-necked round bottom flask was charged with estriol (20. g, 70 mmol) and imidazole (20 g, 0.29 mol). 0.5 L anhydrous DMF was added, and the flask was equipped with an overhead stirrer. The mixture was then stirred, and TBSCl (40 g, 0.265 mol) was added portionwise over ten minutes. The flask was sealed with a nitrogen line. The mixture was homogenous up to 0.5 hour after addition of silyl chloride, after which point a thick white mixture was observed. TLC of the mixture in 1:3 ethyl acetate:hexanes indicated complete, clean conversion of starting material. The mixture was diluted with 0.8 L water, and the resulting precipitate collected by vacuum filtration and washed with 2 L of water. The crude was subjected to flash chromatography using one kg of silica gel, and a 2 to 20% gradient of ethyl acetate in hexanes. 17.1 g (49% yield) of the desired intermediate was obtained and 22.5 g of the tris-silyl-estriol-ether (49% yield) was obtained. $^1$H NMR (300 MHz, CDCl$_3$) δ ppm 7.12 (d, J=8.4 Hz, 1H), 6.61 (dd, J=8.25, 2.70 Hz), 6.55 (d, J=2.40 Hz), 4.13-4.07 (m, 1H), 3.57 (d, J=5.7 Hz), 0.98 (s, 9H), 0.92 (s, 9H), 0.79 (s, 3H), 0.19 (s, 6H), 0.107-0.094 (m, 6H).

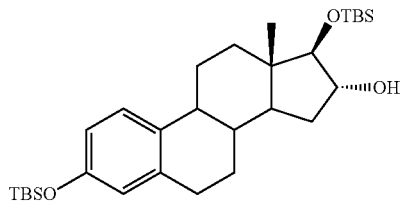 [SMILES: CC(C)(C)[Si](C)(C)Oc1ccc2c(c1)CCC1C2CC[C@@]2(C)C1C[C@@H](O)[C@@H]2O[Si](C)(C)C(C)(C)C]

Synthesis of (13S,16R,17R)-3,17-bis(tert-butyldimethylsilyloxy)-13-methyl-7,8,9,11,12,13,14,15,16,17-decahydro-6H-cyclopenta[a]phenanthren-16-ol 26: A round bottom flask was charged with the tris-silyl-estriol ether (31.5 g, 50 mmol) obtained in the previous step and dissolved in 250 mL DCM and 250 mL acetone. p-TSA (9.5 g, 50 mmol) was added, and the mixture was allowed to stir. After two hours, the reaction was quenched with sodium bicarbonate (it was determined previously on smaller scale that longer reaction times led to more complex product mixtures), and the volatiles were removed under vacuum. The concentrated aqueous was extracted with DCM (3×100 mL). The combined organic layers were washed with brine, and dried over sodium sulfate. The crude material was subjected to flash chromatography using a 5-10% gradient of ethyl acetate in hexanes, affording 16.6 g of the desired intermediate 26 (64% yield). The unreacted starting material was easily recovered for further use. $^1$H NMR (300 MHz, CDCl$_3$), δ 7.11 (d, J=8.7 Hz, 1H), 6.62 (dd, J=8.4 Hz, 2.40 Hz, 1H), 6.56 (d, J=2.40 Hz, 1H), 4.18-4.06 (m, 1H), 3.52 (d, J=5.4 Hz, 1H), 0.98 (s, 9H), 0.93 (s, 9H), 0.77 (s, 3H), 0.19 (s, 6H), 0.12-0.098 (m, 6H).

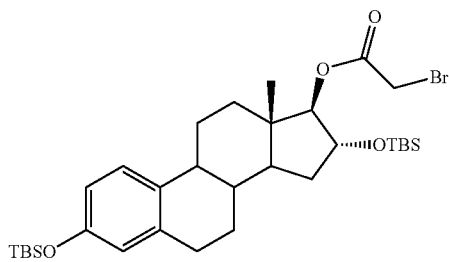 [SMILES: CC(C)(C)[Si](C)(C)Oc1ccc2c(c1)CCC1C2CC[C@@]2(C)C1C[C@@H](O[Si](C)(C)C(C)(C)C)[C@@H]2OC(=O)CBr]

Synthesis of (13S,16R,17R)-3,16-bis(tert-butyldimethylsilyloxy)-13-methyl-7,8,9,11,12,13,14,15,16,17-decahydro-6H-cyclopenta[a]phenanthren-17-yl 2-bromoacetate 27: The procedure followed was that as was described for intermediate 17, with the following exceptions—the acid chloride was distilled prior to use and two equivalents of this material was used in the attempt. The material was isolated using flash chromatography using 2% ethyl acetate in hexanes. The yield was 88%: $^1$H NMR (300 MHz, CDCl$_3$) δ ppm 7.10 (d, 1H), 6.60 (dd, 1H), 6.52 (d, 1H), 4.91 (d, 1H), 4.36 (t, 1H), 3.87 (d, 2H), 0.97 (s, 9H), 0.88 (s, 9H), 0.83 (s, 3H), 0.18 (s, 6H), 0.036 (d, 6H).

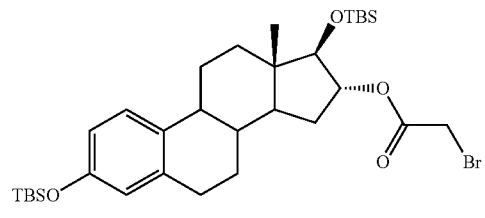 [SMILES: CC(C)(C)[Si](C)(C)Oc1ccc2c(c1)CCC1C2CC[C@@]2(C)C1C[C@@H](OC(=O)CBr)[C@@H]2O[Si](C)(C)C(C)(C)C]

Synthesis of (13S,16R,17R)-3,17-bis(tert-butyldimethylsilyloxy)-13-methyl-7,8,9,11,12,13,14,15,16,17-decahydro-6H-cyclopenta[a]phenanthren-16-yl 2-bromoacetate 28: The procedure followed was that as was described for intermediate 27: $^1$H NMR (300 MHz, CDCl$_3$) δ ppm 7.10 (d, 1H), 6.60 (dd, 1H), 6.52 (d, 1H), 5.04-4.92 (m, 1H), 3.83 (s, 2H), 3.79 (d, 1H), 0.97 (s, 9H), 0.88 (s, 9H), 0.81 (s, 3H), 0.18 (s, 6H), 0.045 (d, J=7.18 Hz, 6H).

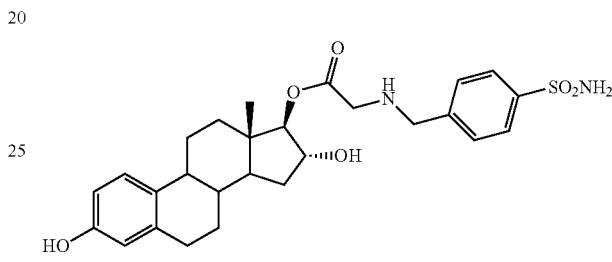

Synthesis of (13S,16R,17R)-3,16-dihydroxy-13-methyl-7,8,9,11,12,13,14,15,16,17-decahydro-6H-cyclopenta[a]phenanthren-17-yl 2-(4-sulfamoylbenzylamino)acetate 27A: A round bottom flask was charged with steroid intermediate 27 (0.96 g, 1.5 mmol), 4-homosulfanilamide HCl (0.67 g, 3.0 mmol), 18-crown-6 ether (20 mg, 0.075 mmol), TBAI (55 mg, 0.15 mmol), potassium carbonate (1.03 g, 7.5 mmol), 4° A molecular sieve (128 mg) and finally 7 mL anhydrous DMF. The mixture was allowed to stir under nitrogen and periodically checked for the reaction progress using TLC (5% EtOAc in hexanes). 48 hours was required for full conversion of steroid intermediate. The mixture was diluted with water (25 mL) and extracted with diethyl ether (50 mL). The organic phase was washed with water (2×50 mL), brine, and dried over sodium sulfate. The solvent was removed under vacuum, leaving 0.98 g of crude material. The desired intermediate was isolated using flash chromatography utilizing 10% acetone in DCM affording 0.48 g (43% yield). The material was then subjected to treatment with TBAF as described, this resulted in removal of the 3-TBS group in 50% yield, another 133 mg of a more polar product was obtained which was revealed to be the desired analog with deblocked 3 and 16 hydroxyl groups (40% yield). The intermediate with the remaining 16-TBS ether was treated with 2 mL of 2 M HCl in 10 mL dioxanes; one hour was required for complete, clean removal of this protecting group as evident by TLC. The mixture was diluted with sodium bicarbonate solution (25 mL) and the aqueous extracted with ethyl acetate. The combined extracts were washed with water (3×50 mL), brine, and dried over sodium sulfate. The product was isolated by flash chromatography using 1:1 acetone in DCM, affording 108 mg of the desired analog 27A (72%): $^1$H NMR (δ, DMSO-d$_6$, 300 MHz): 8.99 (s, 1H), 7.77 (d, ArH 8.34 Hz, 2H), 7.51 (d, J=8.32 Hz, 2H), 7.30 (s, 2H), 7.02 (d, J=11.22 Hz, 1H) 6.50 (dd, J=8.24 Hz, 2.12 Hz, 1H), 6.43 (d, J=2.46 Hz, 1H) 4.92 (d, J=5.38 Hz, 1H), 4.69 (d, J=5.58 Hz, 1H), 4.112-4.089 (m, 1H), 3.809 (s, 2H), 3.413 (s, 2H) 0.714 (s, 3H). IR (cm⁻¹): 3299, 2921, 2858, 1725, 1498, 1448, 1320, 1221, 1158, 818, 676, 587. Optical Rotation: $[\alpha]_D^{20}$=+10 (MeOH).

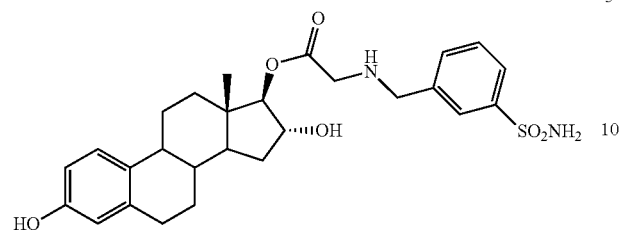

Synthesis of (13S,16R,17R)-3,16-dihydroxy-13-methyl-7,8,9,11,12,13,14,15,16,17-decahydro-6H-cyclopenta[a]phenanthren-17-yl 2-(3-sulfamoylbenzylamino)acetate 28A: The procedure described for analog 14A was followed here (using 3-sulfamoylbenzylamine HCl in this case). The removal of the TBS groups was conducted as such: 386 mg (0.5 mmol) of the 3,16-bis-silyl ether was dissolved in 10 mL of 1,4-dioxanes and 5 mL of 2 M HCl. Clean removal of the protecting groups was observed by TLC within one hour. The reaction was diluted with sodium bicarbonate solution, and extracted with ethyl acetate, which was washed three times with water before getting rid of the solvent under vacuum. The desired analog 28A was purified using flash chromatography utilizing 1:1 acetone:DCM to afford 150 mg (58% yield): ¹H NMR (δ, DMSO-d₆, 300 MHz): 8.99 (s, 1H), 7.82 (s, 1H), 7.71-7.69 (m, 1H), 7.53-7.50 (m, 2H), 7.32 (s, 2H), 7.04 (d, J=11.22 Hz, 1H) 6.50 (dd, J=8.24 Hz, 2.12 Hz, 1H), 6.43 (d, J=2.46 Hz, 1H) 4.92 (d, J=5.78 Hz, 1H), 4.70 (d, J=4.80 Hz, 1H), 4.117-4.074 (m, 2H), 3.81 (bs, 2H), 3.41 (s, 2H) 0.72 (s, 3H). IR (cm⁻¹): 3311, 2917, 2854, 1729, 1498, 1330, 1196, 1146. ESI-MS −513.2 (M−1)⁻, 515.2 (M+1)⁺. Optical Rotation: $[\alpha]_D^{20}$=+3 (MeOH); MP: 90-92.5° C.

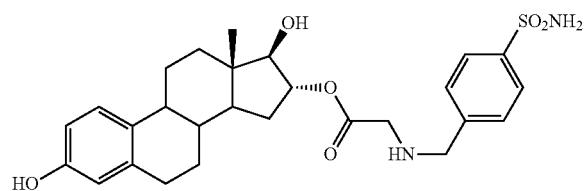 [SMILES: C[C@]12CCC3c4ccc(O)cc4CCC3C1C[C@@H](OC(=O)CNCc1ccc(S(N)(=O)=O)cc1)[C@@H]2O]

Synthesis of (13S,16R,17R)-3,17-dihydroxy-13-methyl-7,8,9,11,12,13,14,15,16,17-decahydro-6H-cyclopenta[a]phenanthren-16-yl 2-(4-sulfamoylbenzylamino)acetate 29A: The procedure for analog 14A was followed here: ¹H NMR (δ, DMSO-d₆, 300 MHz): 9.00 (s, 1H), 7.77 (d, J=8.40 Hz, 2H), 7.50 (d, J=8.40 Hz, 2H), 7.30 (s, 2H), 7.02 (d, J=11.22 Hz, 1H,) 6.50 (dd, J=8.24 Hz, 2.12 Hz, 1H), 6.43 (d, J=4.92 Hz, 1H) 5.04 (d, J=4.98 Hz, 1H), 4.879-4.741 (m, 1H), 3.79 (bs, 2H), 3.580 (t, J=5.44 Hz, 1H), 0.719 (s, 3H). IR (cm⁻¹): 3282, 2921, 2858, 1721, 1330, 1217, 1154. ESI-MS−514.2 (M−1)⁻. Optical Rotation: $[\alpha]_D^{20}$=+17 (MeOH).

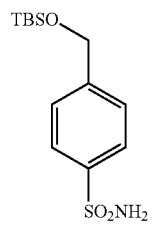

Synthesis of 4-((tert-butyldimethylsilyloxy)methyl)benzenesulfonamide 29: 4-(Hydroxymethyl)benzene-sulfonamide (5.5 g, 30 mmol—from borane reduction of 4-sulfamoylbenzoic acid, as described in JMC, 4522, 2010) was placed in a round bottom flask along with TBSCl (4.9 g, 9.3 mmol) and imidazole (4.1 g, 16.8 mmol) and the reactants dissolved in 25 mL anhydrous DMF. The mixture was allowed to stir under nitrogen and TLC indicated complete conversion of starting material within 2 hours. The mixture was then diluted with 300 mL ethyl acetate and washed with water (5×100 mL), brine, and dried over sodium sulfate, resulting in 10 g of crude as a white semi solid. This was subjected to flash chromatography eluting with a 20 to 30% gradient of ethyl acetate in hexanes to afford the product 29 as a white crystalline solid (7.56 g, 84%): ¹H NMR (300 MHz, CDCl₃) δ ppm 7.90 (d, J=8.44 Hz, 2H), 7.48 (d, J=8.65 Hz, 2H), 4.89-4.73 (m, 4H), 0.95 (s, 9H), 0.12 (s, 6H).

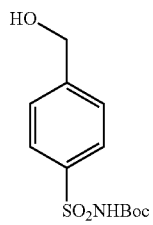

Synthesis of tert-butyl 4-(hydroxymethyl)phenylsulfonylcarbamate 30: A round bottom flask was charged with intermediate 29 (7.55 g, 25 mmol), and DMAP (0.31 g, 2.5 mmol), and dissolved in 75 mL DCM and 4.2 mL TEA (30 mmol) and chilled to 0° C. A separate solution of Boc-anhydride (6.56 g, 30 mmol) in 75 mL DCM was added via addition funnel under nitrogen and the mixture allowed to stir and gradually warm up to room temperature overnight. TLC indicated complete conversion of starting material, and the mixture was diluted with 100 mL of saturated ammonium chloride. The aqueous was then extracted with DCM, and the combined organic layers were washed with brine and dried over sodium sulfate. The crude was then subjected to flash chromatography using 15% ethyl acetate in hexanes to afford the desired material (8.1 g, 80% yield). The TBS group was then removed as described in the general procedure to render the alcohol 30: ¹H NMR: (DMSO-d₆) δ ppm 7.82 (d, J=8.35 Hz, 2H), 7.55 (d, J=8.31 Hz, 2H), 5.42 (bs, 1H), 4.59 (s, 1H), 1.29 (s, 9H).

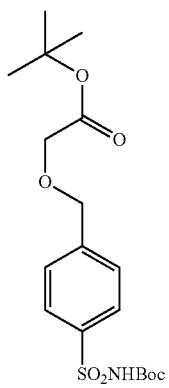

Synthesis of tert-butyl 2-(4-(N-(tert-butoxycarbonyl)sulfamoyl)benzyloxy)acetate 31: A scintillation vial equipped with a rubber septa-screw cap was charged with sodium hydride (50 mg, 60% w/w mineral oil, 1.24 mmol) and suspended in 1 mL anhydrous DMF under nitrogen. The vial was chilled to 0° C., and intermediate 30 (170 mg, 0.59 mmol) in 1 mL DMF was added dropwise to the vial. The mixture was allowed to stir for thirty minutes at cold temperature before the neat addition of t-butyl-bromoacetate (0.1 mL, 0.71 mmol). By two hours time, HPLC analysis indicated complete consumption of intermediate 30. The mixture was treated with 1 mL 0.2M HCl and extracted with ethyl acetate. The crude was subjected to flash chromatography using 5% acetone in DCM, affording 110 mg of the desired intermediate 31 (46%): $^1$H NMR (300 MHz, CDCl$_3$) δ ppm 8.00 (d, J=8.4 Hz, 2H), 7.55 (d, J=8.3 Hz), 4.71 (s, 2H), 4.05 (s, 2H), 1.49 (s, 9H), 1.39 (s, 9H).

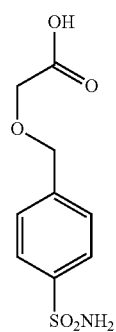

Synthesis of 2-(4-sulfamoylbenzyloxy)acetic acid 32: A scintillation vial was charged with intermediate 31 (0.15 g, 0.37 mmol) and dissolved in 2 mL DCM. TFA (1 mL, 13 mmol) was then added. The mixture was allowed to stir for 5 hours before all volatiles were removed under vacuum. The crude (as a light brown oil) was crystallized from DCM:MeOH:diethyl ether:hexanes (1:0.2:5:10) to afford the product as a white crystalline solid 32 (65 mg, 71% yield), 25 mg of desired product with Boc group still intact obtained from the mother liquor was sole impurity: Product $^1$H NMR (300 MHz, DMSO-d$_6$) δ ppm, 7.80 (d, 8.35 Hz, 2H), 7.52 (d, 8.41 Hz, 2H), 4.62 (s, 2H), 4.11 (s, 2H). IR (cm$^{-1}$) 3395, 3265, 1750, 1318, 1146, 1091, 819, 697, 596.

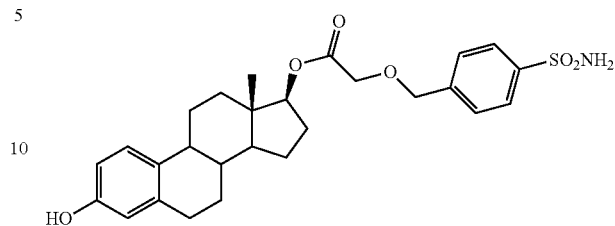

(13S,17S)-3-hydroxy-13-methyl-7,8,9,11,12,13,14,15,16,17-decahydro-6H-cyclopenta[a]phenanthren-17-yl 2-(4-sulfamoylbenzyloxy)acetate 17A: Intermediate 32 (240 mg, 1.02 mmol) was suspended in 1.56 mL of a 1 M solution of DCC in DCM and 10 mL DCM and allowed to stir for thirty minutes before addition of steroid 7 (0.24 g, 0.63 mmol) and DMAP (8 mg, 0.0625 mmol). The mixture was allowed to stir overnight and then diluted with DCM and filtered. The volatiles were removed in vacuo and the desired intermediate was obtained by MPLC using a 0 to 10% gradient of acetone in DCM to afford 65 mg of the desired intermediate. The 3-TBS group was removed by treatment with 2 M HCl (2 mL) in 4 mL of 1,4-dioxanes, monitoring of the reaction by TLC indicated a 6 hour stir for full removal of the TBS group. The final analog 17A was purified using MPLC with a 0 to 20% gradient of acetone in DCM: $^1$H NMR (δ, DMSO-d$_6$, 300 MHz): 9.002 (s, 1H, ArOH), 7.809 (d, 2H, ArH, J=4.20 Hz), 7.532 (d, 2H, ArH, J=4.35 Hz), 7.352 (s, 2H, —SO$_2$NH$_2$), 7.028 (d, 1H, ArH, J=4.16 Hz), 6.497 (dd, 1H, ArH, J=4.12 Hz, 1.06 Hz), 6.454 (d, 1H, ArH, J=0.05 Hz), 4.712 (t, J=5.10 Hz, 1H, —CH), 4.640 (s, 2H, —CH$_2$), 4.233 (s, 2H, —CH$_2$), 0.773 (s, 3H, —CH$_3$). IR (cm$^{-1}$): 3362, 3257, 2917, 2862, 1733, 1595, 1498, 1209, 1154, 831, 671. ESI-MS −498.1 (M−1)$^−$, 517.2 (M+H$_2$O)$^+$. Optical Rotation: [α]$_D^{20}$=+36 (MeOH); MP: 167.5-170.3° C.

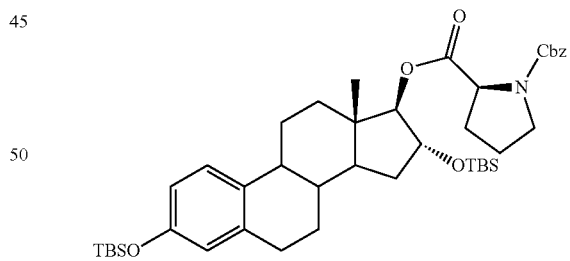

Synthesis of (2S)-1-benzyl 2-((13S,16R,17R)-3,16-bis(tert-butyldimethylsilyloxy)-13-methyl-7,8,9,11,12,13,14,15,16,17-decahydro-6H-cyclopenta[a]phenanthren-17-yl) pyrrolidine-1,2-dicarboxylate 33: The procedure described in scheme 7 was followed here (76% yield): $^1$H NMR (300 MHz, CDCl$_3$) δ ppm 7.40-7.28 (m, 5H), 7.08 (t, J=6.90 Hz, 1H), 6.61 (dd, J=8.10 Hz, 1.80 Hz, 1H), 6.54 (d, J=1.80 Hz, 1H), 5.09 (dd, J=65.25 Hz, 10.5 Hz, 1H), 5.00 (bs, 1H), 4.85 (dd, J=8.7 Hz, 5.4 Hz, 1H), 4.52-4.44 (m, 1H), 4.32-4.24 (m, 1H), 3.65-3.56 (m, 2H), 0.97 (s, 9H), 0.92-0.85 (m, 10H), 0.71 (d, J=2.1 Hz, 3H), 0.18 (s, 6H), 0.10-0.01 (m, 6H).

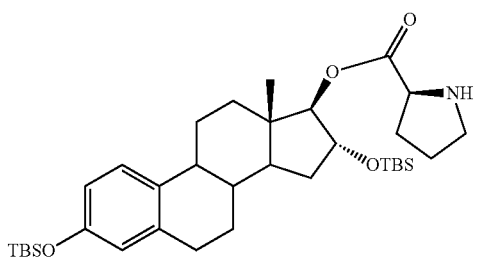 [SMILES: CC(C)(C)[Si](C)(C)Oc1ccc2c(c1)CCC1C2CC[C@@]2(C)C1C[C@@H](O[Si](C)(C)C(C)(C)C)[C@@H]2OC(=O)[C@@H]1CCCN1]

Synthesis of (2S)-((13S,16R,17R)-3,16-bis(tert-butyldimethylsilyloxy)-13-methyl-7,8,9,11,12,13,14,15,16,17-decahydro-6H-cyclopenta[a]phenanthren-17-yl) pyrrolidine-2-carboxylate 34: The procedure described in scheme 7 was followed here (96% yield): $^1$H NMR (300 MHz, CDCl$_3$) δ ppm 7.09 (d, J=8.40 Hz, 1H), 6.60 (dd, 7.65 Hz, 2.4 Hz, 1H), 6.54 (d, 1.80 Hz), 4.88 (d, J=5.7 Hz, 1H), 4.35-4.28 (m, 1H), 3.84-3.77 (m, 1H), 3.16-3.08 (m, 1H), 2.96-2.88 (m, 1H), 0.97 (s, 9H), 0.87 (s, 9H), 0.79 (s, 3H), 0.18 (s, 6H), 0.033-0.016 (m, 6H).

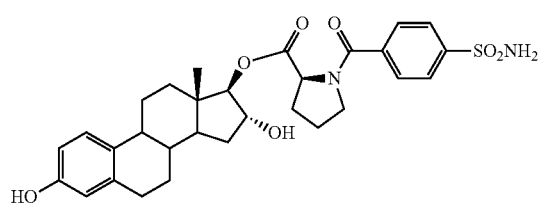 [SMILES: C[C@]12CCC3c4ccc(O)cc4CCC3C1C[C@@H](O)[C@@H]2OC(=O)[C@@H]1CCCN1C(=O)c1ccc(S(N)(=O)=O)cc1]

[(13S,16R,17R)-3,16-dihydroxy-13-methyl-6,7,8,9,11,12,14,15,16,17-decahydrocyclopenta[a]phenan-thren-17-yl] (2S)-1-(4-sulfamoylbenzoyl) pyrrolidine-2-carboxylate 30A: The procedure for coupling 4-sulfamoylbenzoic acid to intermediate 34 was the same as described in scheme 7 (57% yield). The bis TBS analog of 30A (1.8 g, 2.26 mmol) was dissolved in 45 mL of 1,4-dioxanes and 22 mL of 2 M HCl was added. TLC (1:4 acetone:DCM) indicated complete deprotection within 2 hours. The mixture was transferred to an Erlenmeyer flask, and treated with saturated sodium bicarbonate solution portionwise until the pH was neutral. The aqueous was extracted with ethyl acetate, and the final analog 30A was isolated using MPLC (0 to 50%) acetone in DCM, 652 mg obtained (51% yield): $^1$H NMR (300 MHz, DMSO-d$_6$) δ 9.02 (s, 1H), 8.02-7.88 (m, 2H), 7.79-7.66 (m, 2H), 7.50 (s, 2H), 7.02 (d, J=8.4 Hz, 1H), 6.50 (d, J=8.5 Hz, 1H), 6.43 (s, 1H), 4.64-4.52 (m, 1H), 4.17 (s, 1H), 3.52 (s, 1H), 0.71 (s, 3H). IR (cm$^{-1}$): 1737, 1611, 1444, 1339, 1158, 710, 613. ESI-MS: 567.2 (M−1)$^-$; 569.2 (M+1)$^+$. Optical Rotation: [α]$_D^{20}$=−30 (MeOH); MP: 243.0-245.5° C.

Synthesis of (S)-1-(4-sulfamoylphenyl)pyrrolidine-2-carboxylic acid 35: A round bottom flask was charged with 4-fluorobenzenesulfonamide (945 mg, 5.4 mmol), L-proline-t-butyl ester HCl (1.24 g, 6 mmol), and cesium carbonate (4.2 g, 12 mmol) and suspended in 10 mL anhydrous DMSO. The mixture was placed in a preheated oil bath and equipped with a condenser, and heated under nitrogen at 168° C. overnight. HPLC analysis of the mixture indicated complete conversion of the benzenesulfonamide starting material. The mixture was transferred to an Erlenmeyer flask, the reaction pot was diluted with 2 mL of concentrated HCl, and added to the mixture in the Erlenmeyer flask and allowed to stir. The aqueous was then extracted with ethyl acetate (3×50 mL), and the combined extracts were washed with water (3×15 mL). The volatiles were then removed under vacuum, and 1.24 g of crude material was obtained. The desired intermediate was isolated using MPLC, utilizing a 0 to 60% gradient of acetone in DCM, affording 35 (0.56 g, 41%): $^1$H NMR (300 MHz, DMSO-d$_6$) δ ppm 7.58 (d, J=9.0 Hz, 2H), 6.98 (s, 2H), 6.54 (d, J=9.0 Hz, 2H), 4.28 (d, J=8.4 Hz, 1H), 2.35-2.22 (m, 2H), 2.04-1.96 (m, 2H).

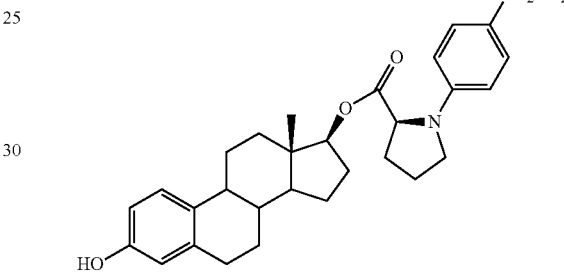

[(13S,17S)-3-hydroxy-13-methyl-6,7,8,9,11,12,14,15,16,17-decahydrocyclopenta[a]phenanthren-17-yl] 1-(4-sulfamoylphenyl)pyrrolidine-2-carboxylate 22A: Steroid 7 was coupled with intermediate 35 as described in scheme 7 (69% yield). The 3-TBS group was removed as described previously (62%): $^1$H NMR (300 MHz, DMSO-d$_6$) δ 9.02 (s, 1H), 7.67-7.56 (m, 2H), 7.14-6.93 (m, 3H), 6.61-6.39 (bs, 4H), 4.60 (t, J=9.7 Hz, 1H), 4.47-4.38 (m, 1H), 0.73 (s, 2H), 0.65 (s, 1H)—last 2 shifts represent the 19-methyl as rotamers. IR (cm$^{-1}$): 3374, 3252, 1725, 1704, 1591, 1146, 1095, 814, 605. ESI-MS 523.2 (M−1)$^-$. Optical Rotation: [α]$_D^{20}$=+50 (MeOH).

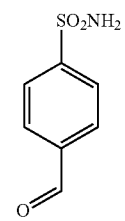

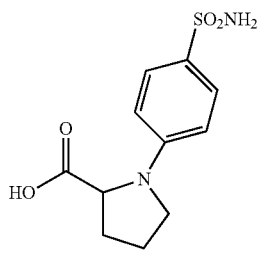 [SMILES: NS(=O)(=O)c1ccc(N2CCCC2C(=O)O)cc1]

Synthesis of 4-formylbenzenesulfonamide 36: A round bottom flask was charged with 4-hydroxymethylbenzenesulfonamide (3.75 gm 20 mmol). 40 g of activated molecular sieves were added, and then 150 mL THF. 37.6 g (0.1 mol) of PDC was then added, and the mixture was allowed to stir for 2 hours, following which time TLC in 1:1 acetone:DCM indicated complete conversion of starting material. The mixture was filtered through a plug of silica, and eluted with acetone. The solvents were removed under vacuum, and the desired material obtained by MPLC using a 0 to 60% ethyl acetate gradient in hexanes, affording 36 (2.05 g, 55%). $^1$H NMR (300 MHz, DMSO-d$_6$) δ ppm 10.09 (s, 1H), 8.20-7.93 (m, 4H), 7.61 (s, 2H).

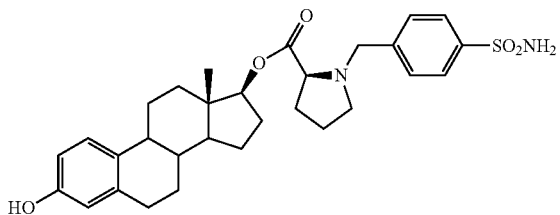 [SMILES: C[C@]12CCC3c4ccc(O)cc4CCC3C1CC[C@@H]2OC(=O)[C@@H]1CCCN1Cc1ccc(S(N)(=O)=O)cc1]

[(13S,17S)-3-hydroxy-13-methyl-6,7,8,9,11,12,14,15,16,17-decahydrocyclopenta[a]phenanthren-17-yl] 1-[(4-sulfamoylphenyl)methyl]pyrrolidine-2-carboxylate 23A: A round bottom flask was charged with aldehyde 36 (2.0 g, 10.8 mmol), and sodium cyanoborohydride (0.45 g, 7.2 mmol). 100 mL THF was added, then 0.41 mL AcOH (7.2 mmol). A proline-E2-3-TBS intermediate made as described in scheme 7 was added (3.49 g, 7.2 mmol) and 300 mg of activated molecular sieves. The mixture was allowed to stir under nitrogen overnight. Following quench with ammonium chloride solution and neutralization with sodium bicarbonate solution and extraction with ethyl acetate, an initial attempt to isolate the desired intermediate by chromatography was unsuccessful at removing the excess aldehyde used in the reaction. The material was then treated suspended in 10 ml of THF and 1 ml of MeOH and chilled to 0° C., and treated with 50 mg of sodium borohydride. After this treatment, intermediate was easy to isolate by MPLC (0 to 16% acetone gradient in DCM). The TBS group was removed in the usual manner $^1$H NMR (300 MHz, DMSO-d$_5$) δ 9.02 (s, 1H), 7.76 (d, J=6.6 Hz, 2H), 7.49 (d, J=8.6 Hz, 2H), 7.32 (s, 2H), 7.03 (d, J=6.4 Hz, 1H), 6.50 (dd, J=8.0, 2.1 Hz, 1H), 6.43 (d, J=2.0 Hz, 1H), 4.73-4.58 (m, 1H), 3.98 (d, J=14.6 Hz, 1H), 3.59 (d, J=13.8 Hz, 1H), 0.77 (s, 3H). IR (cm$^{-1}$): 3257, 2921, 2850, 1721, 1326, 1158, 684, 575. ESI-MS 537.3 (M−1)$^-$; 539.2 (M+1)$^+$. Optical Rotation: [α]$_D^{20}$=−2 (MeOH).

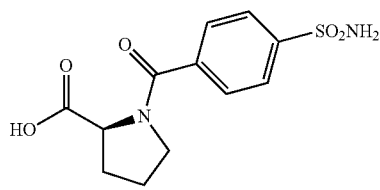 [SMILES: NS(=O)(=O)c1ccc(C(=O)N2CCC[C@H]2C(=O)O)cc1]

Synthesis of (S)-1-(4-sulfamoylbenzoyl)pyrrolidine-2-carboxylic acid 37: L-Proline (12.4 g, 0.108 mol) was suspended in 50 mL of methanol, and the mixture was cooled in an ice bath. Thionyl chloride (8.1 mL, 0.11 mol) was added dropwise over twenty minutes. At the end of the addition, the now homogenous mixture was removed from the ice bath, and allowed to stir for two hours before removal of all volatiles under vacuum, affording 19.43 grams of L-proline methyl ester which was used without any further purification.

L-Proline methyl ester (14.8 g, 86.3 mmol) was placed in a round bottom flask along with 4-sulfamoylbenzoic acid (15.6 g, 77.7 mmol). DMF was added (75 mL), then HOBt (14.3 g, 93 mmol) and EDCI (20.7 g, 108 mmol). The mixture was allowed to stir under nitrogen overnight, at which point TLC indicated near complete conversion of starting material. The mixture was then placed into 2.5 L of water, and chilled at 4° C. overnight. The next day crystals were collected and washed with water (2×100 mL). The methyl ester crystals (23 g) were collected, and these were subjected to a second crystallization from sodium bicarbonate. The product crystals were collected (11.4 g, 47% yield).

The methyl ester (10.3 g, 33 mmol) was saponified with sodium hydroxide (13.2 g, 0.33 mol) in water (200 mL) and THF (100 mL). TLC in 1:4 acetone:DCM indicated complete conversion of starting material (following acidification and extraction of an aliquot from the reaction mixture). The pH of the mixture was brought down to 7 using 2 M HCl, then the THF was removed under vacuum. The pH was then brought down to 0 using conc. HCl, and extracted with ethyl acetate. The combined extracts were dried over sodium sulfate, and the volatiles removed affording the acid 37 as a white solid (7.82 g, 80% yield): $^1$H NMR (300 MHz, DMSO-d$_6$): δ (complex aromatic region, due to rotamers) 7.94-7.81 (m, 2H), 7.70-7.54 (m, 2H), 7.49 (bs, 2H), 4.47-4.34 (m, 1H), 3.08-2.93 (m, 1H), 2.37 (m, 1H), 1.93-1.86 (m, 2H). IR (cm$^{-1}$): 3395, 3290, 1725, 1586, 1560, 1441, 1343, 1167, 835, 705. Optical Rotation: [α]$_D^{20}$=−80 (MeOH).

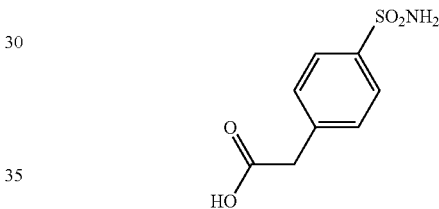

Synthesis of 2-(4-sulfamoylphenyl)acetic acid 38: The procedure as described in PCT Int. Appl., 2013029338, 7 Mar. 2013 was followed: $^1$H NMR (300 MHz, DMSO-d$_6$): δ 7.77 (d, J=7.5 Hz, 2H), 7.45 (d, J=7.8 Hz, 2H), 7.34 (bs, 2H), 3.70 (bs, 2H).

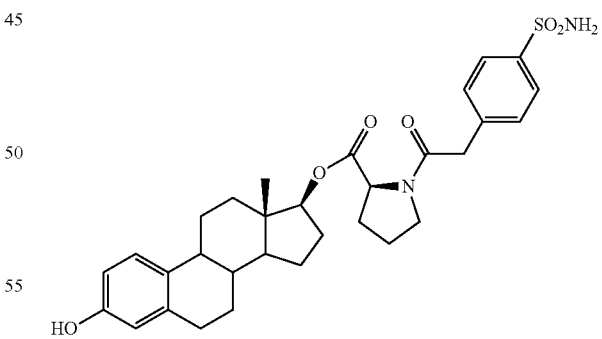

(2S)-((13S,17S)-3-hydroxy-13-methyl-7,8,9,11,12,13,14,15,16,17-decahydro-6H-cyclopenta[a]phenan-thren-17-yl) 1-(2-(4-sulfamoylphenyl)acetyl)pyrrolidine-2-carboxylate 31A: A round bottom flask was charged with proline-E2-3-TBS (made as described in scheme 7, 1.15 g, 2.38 mmol), 38 (1.03 g, 4.77 mmol), and HOBt (730 mg, 4.77 mmol). The solids were dissolved in DMF before addition of EDCI (1.14 g, 5.95 mmol), and allowed to stir under nitrogen for 18 hours at which time, TLC indicated complete conversion of starting material. The mixture was then diluted with water, which caused the desired product to precipitate. 1.51 grams (93% yield) of the desired intermediate was recovered, and the 3-TBS group was removed in the described manner: $^1$H NMR (300 MHz, DMSO-d$_6$): δ 9.01 (bs, 1H), 7.76-7.68 (m, 2H), 7.50-7.30 (m, 4H), 7.04 (d, J=8.1 Hz, 1H), 6.50 (dd, J=8.6, 2.4 Hz, 1H), 6.43 (bs, 1H), 4.73-4.58 (m, 1H), 4.35-4.28 (m, 1H) 3.78 (bs, 2H), 0.78-0.71 (m, 3H). IR (cm$^{-1}$): 3244, 1725, 1624, 1439, 1339, 1188, 1154, 663, Optical Rotation: $[α]_D^{20}$=−36 (MeOH).

HPLC indicated about 50% conversion of testosterone, and the mixture was then diluted in 2.5 L of water, which afforded 1 g of solid after filtration, washing with water and drying under vacuum. The desired product 33A was then obtained by MPLC, using a 0 to 30% gradient of acetone in DCM: $^1$H NMR (300 MHz, DMSO-d$_6$) δ 7.98-7.81 (m, 2H), 7.75-7.65 (m, 2H), 7.49 (bs, 1H), 5.63 (bs, 1H), 4.66-4.44 (m, 2H), 0.86-0.76 (m, 6H). IR (cm$^{-1}$): 3244, 1733, 1613, 1427, 1334, 1161, 608. ESI-MS, 569.3 (M+H)$^+$, Optical Rotation: $[α]_D^{20}$=+56 (MeOH).

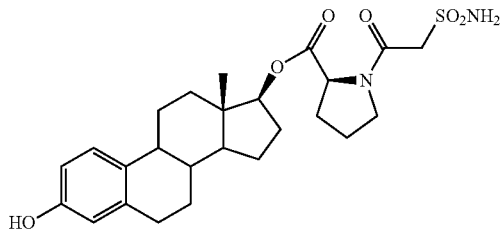 [SMILES: C[C@]12CCC3c4ccc(O)cc4CCC3C1CC[C@@H]2OC(=O)[C@@H]1CCCN1C(=O)CS(N)(=O)=O]

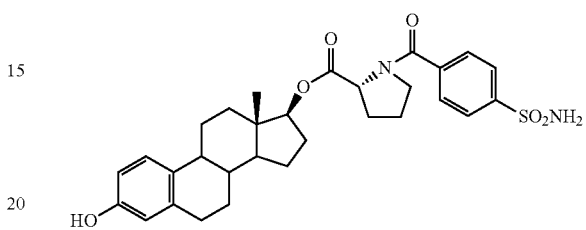

(2S)-((13S,17S)-3-hydroxy-13-methyl-7,8,9,11,12,13,14,15,16,17-decahydro-6H-cyclopenta[a]phenan-thren-17-yl) 1-(2-(4-sulfamoylphenyl)acetyl)pyrrolidine-2-carboxylate 32A: A round bottom flask was charged with chlorosulfonylacetyl chloride (0.3 mL, 2.8 mmol), and dissolved in DCM (2 mL). The solution was chilled to −78° C., and then a solution of E2-proline 1 (1.14 g, 2.36 mmol) in DCM (8 mL) was added dropwise over 15 min. The mixture was allowed to stir for 1.5 hours before addition of ammonium hydroxide solution (28-30%, 1 mL, 14 mmol). The mixture was allowed to stir overnight, gradually assuming room temperature. The next day, TLC confirmed complete conversion of starting material, and the mixture was diluted with 25 mL of 2M HCl. The aqueous was then extracted with ethyl acetate, and the combined organic layers were dried with sodium sulfate. The crude was then subjected to MPLC, using a 0 to 36% gradient of acetone in DCM, affording 318 mg of the desired intermediate, which was then deprotected in the usual manner to afford the desired product 32A: $^1$H NMR (300 MHz, DMSO-d$_6$) δ 9.01 (bs, 1H), 7.68 (bs, 1H), 7.40 (bs, 1H), 7.03 (d, J=8.4 Hz, 1H), 6.50 (dd, J=8.4, 1.8 Hz, 1H), 6.43 (bs, 1H), 4.67 (t, J=7.5 Hz, 1H), 4.41 (dd, J=8.6, 2.7 Hz, 1H), 4.10 (d, J=13.8 Hz, 1H), 3.96 (d, J=13.8 Hz, 1H), 0.79 (s, 3H). IR (cm$^{-1}$): 3437, 3336, 3202, 1729, 1670, 1607, 1334, 1200, 1137. Optical Rotation: $[α]_D^{20}$=−12 (MeOH).

(2R)-((13S,17S)-3-hydroxy-13-methyl-7,8,9,11,12,13,14,15,16,17-decahydro-6H-cyclopenta[α]phenanthren-17-yl) 1-(4-sulfamoylbenzoyl)pyrrolidine-2-carboxylate was synthesized by following the methods in scheme 7 using N-Cbz-D-proline to afford the desired product as white solid 34A (0.45 g): $^1$H NMR (δ, acetone-d$_6$ 300 MHz): 7.97 (d, 2H, ArH, J=8.4 Hz), 7.93 (s, 1H, ArOH), 7.73 (d, 1.6H rotamer, ArH, J=8.1 Hz), 7.61 (d, 0.4H rotamer, ArH, J=8.4 Hz), 7.09 (d, 1H, ArH, J=8.1 Hz), 6.70 (bs, 2H, NH$_2$), 6.59 (m, 1H, ArH), 6.53 (s, 1H, ArH), 4.73 (t, 1H, 17-CH), 4.56 (m, 1H, CH), 0.90 (s, 3H, CH$_3$). IR (cm$^{-1}$): 3248, 2922, 2875, 1737, 1725, 1611. Optical Rotation: $[α]_D^{24}$=+46.5 (c=0.58, 1,4-dioxane). Exemplary compounds were tested for: oral biological activity (Table 1); binding to human carbonic anhydrase II (hCA 2) (Table 2); and, for some compounds enzymatic saponification (Table 3).

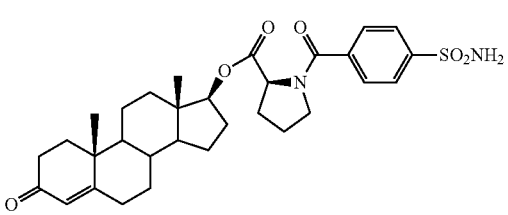 [SMILES: C[C@]12CCC(=O)C=C1CCC1C2CC[C@@]2(C)C1CC[C@@H]2OC(=O)[C@@H]1CCCN1C(=O)c1ccc(S(N)(=O)=O)cc1]

(2S)-((10R,13S,17S)-10,13-dimethyl-3-oxo-2,3,6,7,8,9,10,11,12,13,14,15,16,17-tetradecahydro-1H-cyclopenta[a]phenanthren-17-yl) 1-(4-sulfamoylbenzoyl)pyrrolidine-2-carboxylate 33A: A round bottom flask was charged with testosterone (0.96 g, 3.33 mmol), the acid 37 (2.98 g, 10 mmol), and DMAP (41 mg, 0.33 mmol). The mixture was dissolved in DMF (25 mL), and EDCI was then added (1.92 g, 10 mmol), and the mixture was allowed to stir overnight.

TABLE I

| % Uterine Weight Increase compared to Vehicle: | | |
|---|---|---|
| Compound # | 10.0 μg | 30.0 μg |
| E2 | 118 | |
| EE | 154.2 | |
| J995 | | 203 |
| 1A | | 212 |
| 3A | | 197 |
| 4A | | 164 |
| 5A | | 171 |
| 6A | 152 | |
| 7A | 108 | |
| 8A | 250 | |
| 9A | 218 | |
| 10A | 177 | |
| 11A | 170 | |
| 12A | | 271 |
| 13A | | 136.5 |
| 14A | | 186.6 |
| 15A | | 151.5 |
| 16A | | 313.9 |
| 17A | | 132.9 |
| 18A | 209.1 | |
| 19A | 267.2 | |
| 20A | 97.1 | |
| 21A | 116.8 | |
| 22A | 91.6 | |
| 23A | 272.2 | |

E2, EE, J995 (U.S. Pat. No. 5,705,495, EP 127 35 90 and EP 128 42 73) & 1A (U.S. Pat. No. 7,507,725 and EP 1 294 402 are standard compounds from literatures).

TABLE II

Human Carbonic Anhydrase II Inhibitions:

| Compound # | hCAII (IC50 nM) |
|---|---|
| J995 | 295 |
| 1A | 258 |
| 2A | 3500 |
| 3A | 250 |
| 4A | 450 |
| 5A | 42 |
| 6A | 65 |
| 7A | 300 |
| 8A | 110 |
| 9A | 85 |
| 10A | 510 |
| 11A | 310 |
| 12A | 250 |
| 13A | 500 |
| 14A | 450 |
| 15A | 105 |
| 16A | >10000 |
| 17A | 125 |
| 18A | 203 |
| 19A | 202 |
| 20A | 232 |
| 21A | 100 |
| 22A | 198 |
| 23A | 129 |

Ref: J Biomol Screen. 2006 October; 11(7): 782-91.

TABLE III

Saponification under Plasma/Esterase or Release of Estradiol (E2):

| Compound # | Plasma/Esterase (% E2 release, 10 min) |
|---|---|
| 1A | 95 |
| 3A | 56 |
| 6A | 87 |
| 8A | 83 |
| 9A | 46 |
| 10A | 57 |
| 12A | 70 |
| 16A | 73 |
| 18A | 84 |
| 19A | 89 |
| 20A | 97 |
| 21A | 75 |
| 22A | 91 |
| 23A | 86 |

Ref:
i) J Endocrinol. 1976 October; 71(1): 77-85.
ii) Clinical guide to laboratory tests, 3$^{rd}$ edition, W.B.. Saunders, Co., Philadelphia, 1995: 216-217

Some of the tested compounds show higher oral activity than the parent drug and the other known prodrug candidates such as J=995 and A1. It was also observed that high biological activity via oral dose doesn't seem to depend on binding to hCA2.

Whereas the standard compound J=995 and other compounds like 8A bind very strongly to hCA 2 with IC 50's of 295 and 110 nM respectively, 16A doesn't bind at all with a IC 50 of 10000 nm but shows a comparable high oral activity that J=995 and A8.

Compounds of the invention according to formula (II) are found to be potent and highly bioavailable in the Allan Doisy test in ovarectomized female rats (Walter Eiger et. Al J. Steroid Biochem. Molec Biol. Vol 55 395-403 1995) and in rat PK model. Good properties of these compounds that set them apart from the competition are due to solubility, excellent absorption, as prodrugs that provide good oral exposure. The advantage of the (acid)-(linker) provides the freedom to manipulate the chemical stability of the ester bond between the active ingredients and (acid)-(linker) moieties in such a way that it is not very weak or strong depending on the alpha-substitution of the acid resulting in surprisingly excellent therapeutic outcome (8A).

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A compound of structural formula I:

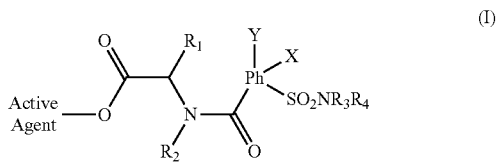

$R_1$ is H, alkyl, cycloalkyl, aryl, alkyl-aryl;

$R_2$ is H or alkyl; or $R_1$ and $R_2$ can be linked together to form a cycloaklyl, or a 3-7 membered ring with up to one heteroatom;

X and Y are each independently H, halogen, cyano, hydroxy, alkoxy, alkyl, aryl, heteroaryl Ar is "phenyl"; and Active Agent is selected from the group consisting of:

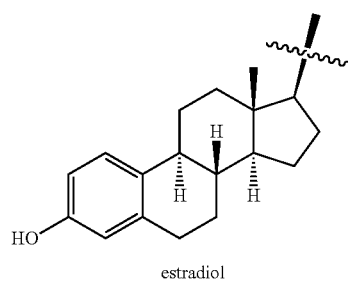

estradiol

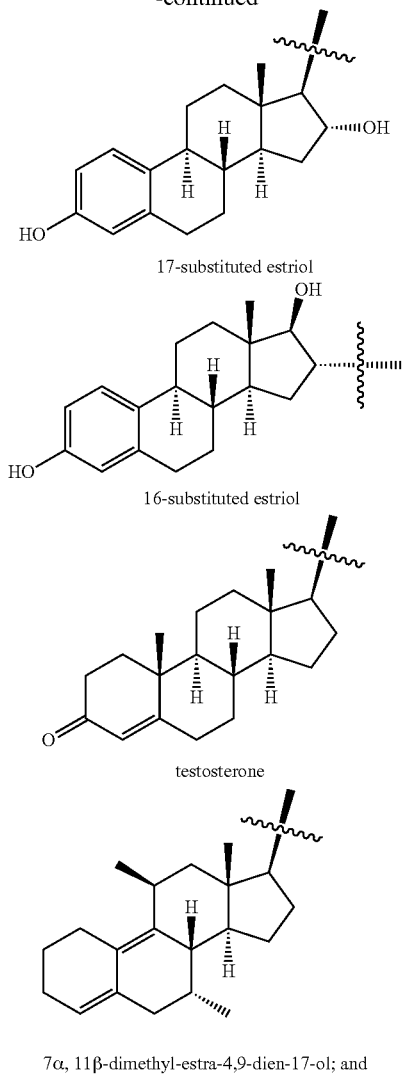

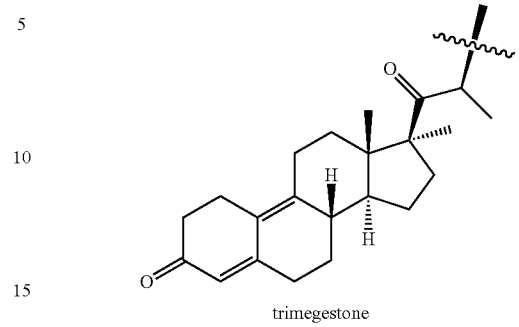

trimegestone

2. The compound of claim 1, wherein the active agent is testosterone.

3. The compound of claim 1, wherein the active agent is 7α, 11β-dimethyl-estra-4, 9-dien-17β-ol.

4. The compound of claim 1, wherein the active agent is estradiol.

5. The compound of claim 1, wherein the active agent is estriol.

6. The compound of claim 1, wherein the active ingredient is trimesgestone.

7. The compound of claim 1, wherein $R_1$ is alkyl.

8. The compound of claim 7, wherein $R_2$ is H; Y and X are H; and $R_3$ and $R_4$ are H.

9. The compound of claim 7, wherein $R_1$ is isopropyl.

10. The compound of claim 7, wherein $R_1$ is methyl.

11. A pharmaceutical composition comprising a compound as described in claim 1 and one or more pharmaceutically acceptable carriers.

* * * * *